US012241176B2

(12) United States Patent
Shearman et al.

(10) Patent No.: US 12,241,176 B2
(45) Date of Patent: *Mar. 4, 2025

(54) SYSTEM AND METHOD FOR GENERATING SYNTHETIC DIAMONDS VIA ATMOSPHERIC CARBON CAPTURE

(71) Applicant: Impossible Diamond, Inc., New York, NY (US)

(72) Inventors: Ryan Shearman, New York, NY (US); Dan Wojno, New York, NY (US); Anthony Ippolito, New York, NY (US)

(73) Assignee: Impossible Diamond, Inc., New York, NY (US)

( * ) Notice: Subject to any disclaimer, the term of this patent is extended or adjusted under 35 U.S.C. 154(b) by 111 days.

This patent is subject to a terminal disclaimer.

(21) Appl. No.: 17/826,685

(22) Filed: May 27, 2022

(65) Prior Publication Data
US 2022/0290325 A1    Sep. 15, 2022

Related U.S. Application Data

(63) Continuation of application No. 17/314,012, filed on May 6, 2021, now Pat. No. 11,585,011, and a
(Continued)

(51) Int. Cl.
*C30B 29/04* (2006.01)
*C01B 32/25* (2017.01)
(Continued)

(52) U.S. Cl.
CPC .............. *C30B 29/04* (2013.01); *C01B 32/25* (2017.08); *C07C 1/12* (2013.01); *C07C 7/144* (2013.01);
(Continued)

(58) Field of Classification Search
CPC ....... C30B 29/04; C30B 35/007; C30B 25/00; C01B 32/25; C01B 32/50; C01B 32/26;
(Continued)

(56) References Cited

U.S. PATENT DOCUMENTS

| 11,371,162 B2 * | 6/2022 | Shearman | ............... C01B 32/26 |
| 11,585,011 B2 * | 2/2023 | Shearman | ............... C01B 32/26 |
| 11,585,012 B2 * | 2/2023 | Shearman | ............... C07C 7/144 |

* cited by examiner

*Primary Examiner* — Thuan D Dang
(74) *Attorney, Agent, or Firm* — Run8 Patent Group, LLC; Peter Miller; Leah Raddatz

(57) ABSTRACT

One variation of a method includes: ingesting an air sample captured during an air capture period at a target location for collection of a first mixture including carbon dioxide and a first concentration of impurities; conveying the first mixture through a liquefaction unit to generate a second mixture including carbon dioxide and a second concentration of impurities less than the first concentration of impurities; in a methanation reactor, mixing the second mixture with hydrogen to generate a first hydrocarbon mixture comprising a third concentration of impurities comprising nitrogen, carbon dioxide, and hydrogen; conveying the first hydrocarbon mixture through a separation unit configured to remove impurities from the first hydrocarbon mixture to generate a second hydrocarbon a fourth concentration of impurities less than the third concentration of impurities; and depositing the second hydrocarbon mixture in a diamond reactor containing a set of diamond seeds to generate a first set of diamonds.

16 Claims, 6 Drawing Sheets

Related U.S. Application Data continuation of application No. 17/314,018, filed on May 6, 2021, now Pat. No. 11,371,162.

(60) Provisional application No. 63/020,980, filed on May 6, 2020.

(51) Int. Cl.
| | |
|---|---|
| *C07C 1/12* | (2006.01) |
| *C07C 7/144* | (2006.01) |
| *C30B 25/00* | (2006.01) |
| *C01B 32/50* | (2017.01) |
| *C07C 1/02* | (2006.01) |
| *E04H 1/12* | (2006.01) |
| *G03B 15/00* | (2021.01) |

(52) U.S. Cl.
CPC .............. *C30B 25/00* (2013.01); *C01B 32/50* (2017.08); *C01P 2006/80* (2013.01); *C07C 1/02* (2013.01); *E04H 1/12* (2013.01); *G03B 15/00* (2013.01)

(58) Field of Classification Search
CPC .. C07C 1/12; C07C 7/144; C07C 9/04; C07C 1/02; C01P 2006/80; E04H 1/12; G03B 15/00; Y02C 20/40
See application file for complete search history.

US 12,241,176 B2

SYSTEM AND METHOD FOR GENERATING SYNTHETIC DIAMONDS VIA ATMOSPHERIC CARBON CAPTURE

CROSS-REFERENCE TO RELATED APPLICATIONS

This application is a continuation of U.S. patent application Ser. No. 17/314,018, filed on 6 May 2021, and U.S. patent application Ser. No. 17/314,012, filed on 6 May 2021, which claim the benefit of U.S. Provisional Application No. 63/020,980, filed on 6 May 2020, each of which is incorporated in its entirety by this reference.

TECHNICAL FIELD

This invention relates generally to the field of diamond synthesis and more specifically to a new and useful method for transforming atmospheric carbon into diamonds in the field of diamond synthesis.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

As shown in FIGS. 1-6, a method S100 includes: ingesting an air sample captured during an air capture period at a target location for collection of a first mixture (e.g., a low-purity carbon dioxide mixture) from the air sample, the first mixture including carbon dioxide and a first concentration of impurities including nitrogen in Block S110; storing the first mixture in a first container associated with the target location in Block S111; conveying the first mixture through a pressurized unit to promote liquefaction of the first mixture to generate a first exhaust stream including impurities including nitrogen and a second mixture (e.g., a high-purity carbon dioxide mixture) including carbon dioxide and a second concentration of impurities less than the first concentration of impurities in Block S120; in a methanation reactor, mixing the second mixture with a stream of hydrogen to generate a first hydrocarbon mixture (e.g., a low-purity hydrocarbon precursor) including hydrocarbons (e.g., methane) and a third concentration of impurities including nitrogen, carbon dioxide, and hydrogen in Block S130; conveying the first hydrocarbon mixture through a separation unit configured to remove impurities from the first hydrocarbon mixture to generate a second exhaust stream including impurities and a second hydrocarbon mixture (e.g., a high-purity hydrocarbon precursor) including hydrocarbons and a fourth concentration of impurities less than the third concentration of impurities in Block S140; and depositing the second hydrocarbon mixture in a diamond reactor containing a set of diamond seeds to generate a first set of diamonds via chemical vapor deposition in Block S150.

Figure 3:
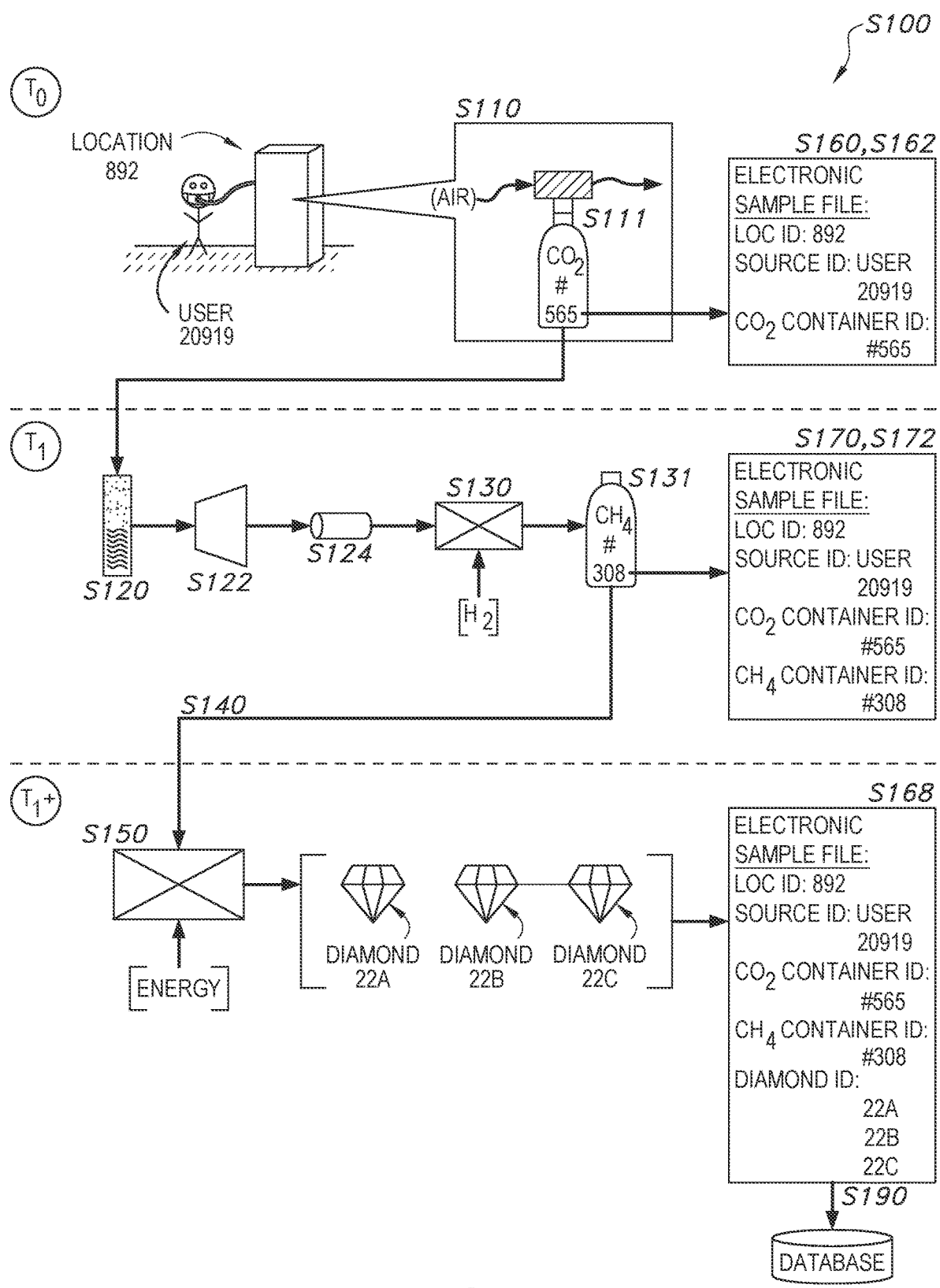
FIG. 3 is a flowchart representation of one variation of the method.
Figure 4:
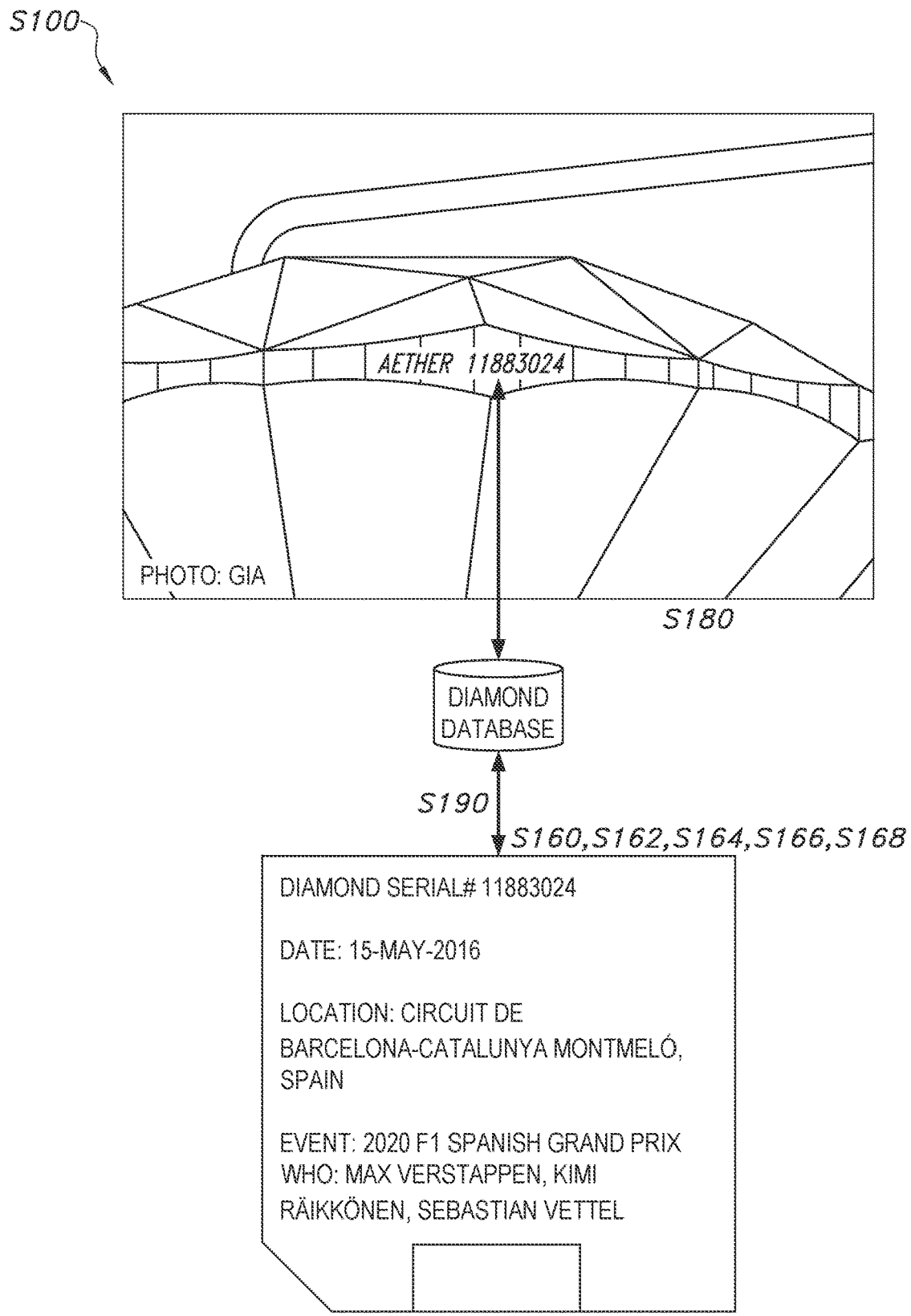
FIG. 4 is a flowchart representation of one variation of the method.

In one variation, as shown in FIGS. 3-6, the method S100 further includes: generating an electronic sample file in Block S160; writing a location identifier for the target location to the electronic sample file in Block S162; and writing a first identifier arranged on the first container to the electronic sample file in Block S170. In another variation, as shown in FIG. 3, the method S100 further includes: storing the second hydrocarbon mixture in a second container associated with the target location in Block S131; and linking a second identifier arranged on the second container to the electronic sample file in Block S172.

In one variation, as shown in FIGS. 3-6, the method S100 further includes: writing a timestamp corresponding to the air capture period to the electronic sample file in Block S164; and writing a source identifier corresponding to a first source of the air sample to the electronic sample file in Block S166.

In another variation, the method S100 further includes: accessing a first diamond identifier assigned to a first diamond, in the first set of diamonds; and writing the first diamond identifier to the electronic sample file in Block S168. In this variation, the method S100 can further include, engraving the first diamond with the first diamond identifier in Block S180.

In one variation, as shown in FIGS. 1-6, the method S100 includes: ingesting an air sample captured during an air capture period at a target location for collection of a first mixture from the air sample, the first mixture including carbon dioxide and a first concentration of impurities including nitrogen in Block S110; conveying the first mixture through a pressurized unit to promote liquefaction of the first mixture to generate a second mixture including carbon dioxide and a second concentration of impurities less than the first concentration of impurities in Block S120; in a methanation reactor, mixing the second mixture with a stream of hydrogen to generate a first hydrocarbon mixture including hydrocarbons and a third concentration of impurities including carbon dioxide and hydrogen in Block S130; conveying the first hydrocarbon mixture through a separation unit configured to separate impurities from the first hydrocarbon mixture to generate a second hydrocarbon mixture including hydrocarbons and a fourth concentration of impurities less than the third concentration of impurities in Block S140; and depositing the second hydrocarbon mixture in a diamond reactor containing a set of diamond seeds to generate a first set of diamonds in Block S150. In this variation, the method S100 further includes, via a computer system: generating an electronic sample file for the air sample in Block S160; writing a location identifier for the target location to the electronic sample file in Block S162; and writing a diamond identifier corresponding to a first diamond, in the first set of diamonds, to the electronic sample file in Block S168.

In one variation, as shown in FIGS. 1-6, the method S100 includes: ingesting an air sample collected during an air capture period for extraction of a first mixture from the air sample, the first mixture including carbon dioxide and a first concentration of impurities including nitrogen in Block S110; conveying the first mixture through a pressurized unit at temperatures within a first temperature range to promote liquefaction of the first mixture to generate a first exhaust stream including impurities including nitrogen and a second mixture including carbon dioxide and a second concentration of impurities less than the first concentration of impurities in Block S120; in a methanation reactor, mixing the second mixture with a stream of hydrogen to generate a first hydrocarbon mixture including hydrocarbons and a third concentration of impurities including nitrogen, carbon dioxide, and hydrogen in Block S130; conveying the first hydrocarbon mixture through a separation unit configured to remove impurities from the hydrocarbon mixture to generate a second exhaust stream including impurities and a second hydrocarbon mixture including hydrocarbons and a fourth concentration of impurities less than the third concentration of impurities in Block S140; and depositing the final hydrocarbon mixture in a diamond reactor containing a set of diamond seeds to generate a first set of diamonds via chemical vapor deposition in Block S150.

In one variation, as shown in FIGS. 1-6, the method S100 includes: ingesting a first mixture extracted from a first air sample, the first mixture including carbon dioxide and a first concentration of impurities including nitrogen in Block S110; conveying the first mixture through a pressurized unit at temperatures within a first temperature range to promote liquefaction of the first mixture to generate a first exhaust stream including impurities including nitrogen and a second mixture including carbon dioxide and a second concentration of impurities less than the first concentration of impurities in Block S120; in a methanation reactor, mixing the second mixture with a stream of hydrogen to generate a first hydrocarbon mixture including hydrocarbons and a third concentration of impurities including nitrogen, carbon dioxide, and hydrogen in Block S130; conveying the first hydrocarbon mixture through a separation unit configured to remove impurities from the hydrocarbon mixture to generate a second hydrocarbon mixture including hydrocarbons and a fourth concentration of impurities less than the third concentration of impurities in Block S140; and depositing the second hydrocarbon mixture in a diamond reactor containing a set of diamond seeds to generate a first set of diamonds via chemical vapor deposition in Block S150.

In one variation, as shown in FIGS. 1-6, the method S100 includes: ingesting a first air sample collected during an air capture period to extract a first mixture including carbon dioxide and a first concentration of impurities including nitrogen in Block S110; conveying the first mixture through a first liquefaction unit configured to remove impurities from the first mixture to generate a first exhaust stream including impurities including nitrogen and a second mixture including carbon dioxide and a second concentration of impurities less than the first concentration of impurities in Block S120; in a methanation reactor, mixing the second mixture with a stream of hydrogen to generate a first hydrocarbon mixture including hydrocarbons and a third concentration of impurities including nitrogen, carbon dioxide, and hydrogen in Block S130; conveying the first hydrocarbon mixture through a second liquefaction unit configured to remove impurities from the second hydrocarbon mixture to generate a second exhaust stream including impurities and a second hydrocarbon mixture including hydrocarbons and a fourth concentration of impurities less than the third concentration of impurities in Block S140; and depositing the second hydrocarbon mixture in a diamond reactor containing a set of diamond seeds to generate a first set of diamonds via chemical vapor deposition in Block S150.

In one variation, as shown in FIGS. 1-6, the method S100 includes: ingesting a first air sample collected during an air capture period to extract a first carbon dioxide mixture including a first concentration of impurities including nitrogen in Block S110; transferring the first carbon dioxide mixture into a liquefaction unit configured to remove impurities from the first carbon dioxide mixture to generate a first exhaust stream including impurities including nitrogen and a second carbon dioxide mixture including a second concentration of impurities less than the first concentration of impurities in Block S120; in a methanation reactor, mixing the second carbon dioxide mixture with a stream of hydrogen to generate a first hydrocarbon mixture including a third concentration of impurities including carbon dioxide, hydrogen, and water in Block S130; conveying the first hydrocarbon mixture through a set of filters configured to capture impurities including hydrogen and carbon dioxide from the first hydrocarbon mixture to generate a second hydrocarbon mixture including a fourth concentration of impurities less than the third concentration of impurities in Block S140; and depositing the second hydrocarbon mixture in a diamond reactor containing a set of diamond seeds to generate a first set of diamonds via chemical vapor deposition in Block S150.

In one variation, as shown in FIGS. 1-6, a method S100 for generating a diamond includes: extracting a first gaseous mixture of carbon dioxide and impurities from an air source, the gaseous mixture exhibiting a first concentration of carbon dioxide and a first concentration of impurities in Block S110; condensing the first gaseous mixture via liquefaction to generate a liquid mixture of carbon dioxide and impurities, the liquid mixture exhibiting a second concentration of carbon dioxide greater than the first concentration of carbon dioxide and a second concentration of impurities less than the first concentration of impurities in Block S120; converting the liquid mixture to a second gaseous mixture via an expander in Block S122; in a first reactor, exposing the second gaseous mixture to a stream of hydrogen, in the presence of a catalyst, to generate a hydrocarbon precursor via methanation of the second gaseous mixture, the hydrocarbon precursor exhibiting a first concentration of methane, a third concentration of carbon dioxide and a third concentration of impurities in Block S130; and, in a diamond reactor at a set temperature, exposing the hydrocarbon precursor to a diamond seed to generate a diamond via chemical vapor deposition in Block S150.

One variation of the method S100 further includes, prior to exposing the hydrocarbon precursor to the diamond seed in the diamond reactor: condensing the hydrocarbon precursor via liquefaction to increase the first concentration of methane exhibited by the hydrocarbon precursor to a second concentration of methane and reduce the third concentration of impurities to a fourth concentration of impurities in Block S140; converting the hydrocarbon precursor from a liquid state to a gaseous state via an expander in Block S146; and purifying the hydrocarbon precursor via absorption to increase the second concentration of methane exhibited by the hydrocarbon precursor to a third concentration of methane and reduce the fourth concentration of impurities to a fifth concentration of impurities in Block S136.

In one variation, the method S100 further includes, prior to methanation of the second gaseous mixture in the first reactor, cleaning the second gaseous mixture via absorption to decrease the second concentration of impurities and increase the second concentration of carbon dioxide exhibited by the second gaseous mixture in Block S124.

2. Applications

Figure 1:
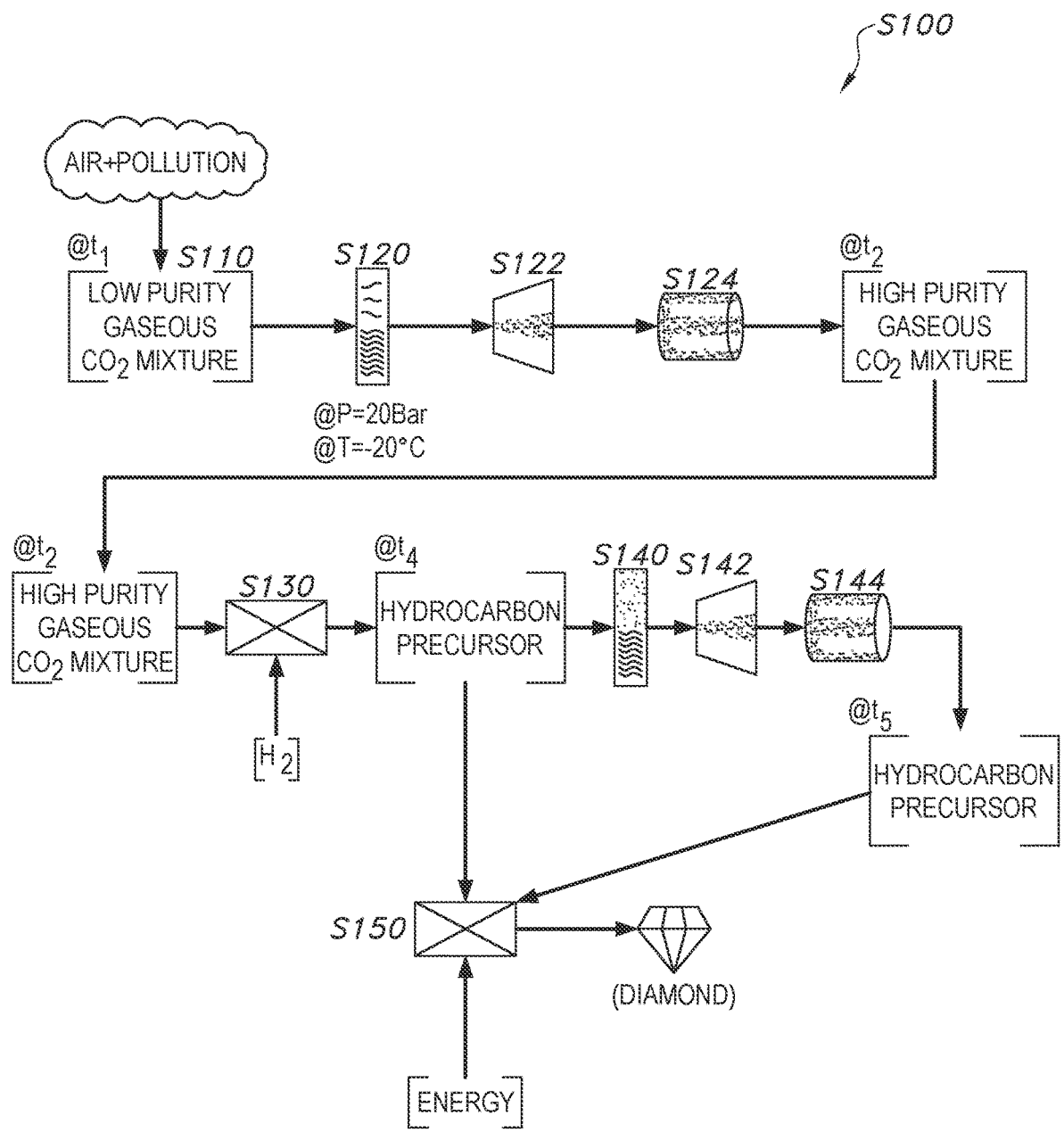
FIG. 1 is a flowchart representation of a method.
Figure 2:
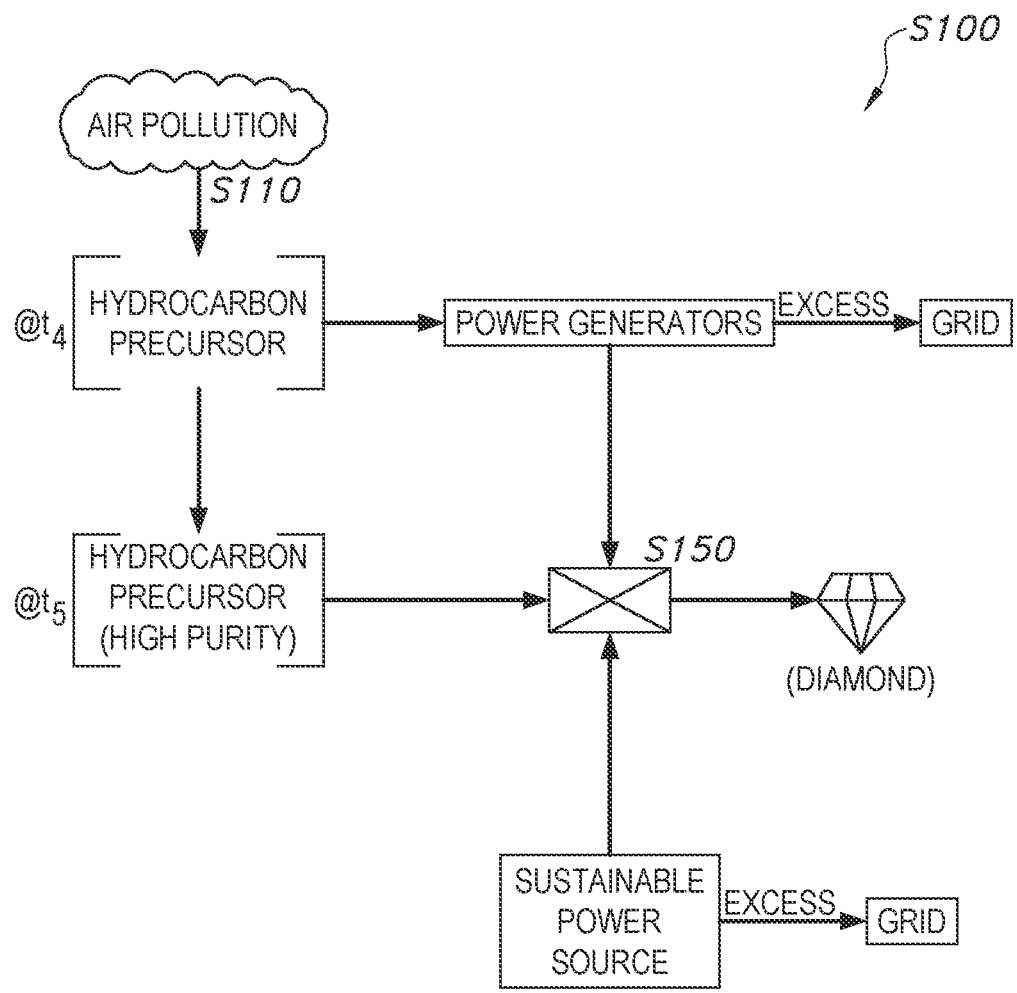
FIG. 2 is a flowchart representation of one variation of the method.

Generally, as shown in FIGS. 1 and 2, the method S100 can be executed: to directly capture a gaseous mixture of carbon dioxide and other components found in air (e.g., Nitrogen, Argon, etc.) from an air source (e.g., re-circulated air within a building, outdoor air, air pollution, human breath); to process this gaseous mixture of carbon dioxide and other components—according to various chemical techniques and/or in combination with additional components—to form a hydrocarbon precursor; and to further react this hydrocarbon precursor to form a diamond product (e.g., a jewelry-grade diamond). In particular, the method S100 includes: harvesting a low-purity carbon dioxide mixture via direct air capture (e.g., via amine filtration) in a known location, at a known time, and/or near known people; transforming this low-purity mixture into a high-purity hydrocarbon precursor via a methanation process; and generating diamond crystals from this high-purity hydrocarbon precursor within a diamond reactor (e.g., a chemical vapor deposition reactor) to produce ethically-sourced, lab-grown, carbon-negative, jewelry-grade diamonds associated with the known location, the known time, and/or the known people. For example, the method S100 can be executed to extract a carbon dioxide mixture from atmospheric air and generate diamonds of sufficient quality (e.g., size, cut, color, etc.) for jewelry (e.g., type IIA diamonds) via a carbon-negative process from this carbon dioxide mixture.

Traditional processes for generating lab-grown diamonds include sourcing hydrocarbons (e.g., fossil fuels) directly from the ground via mining, resulting in generation of pollution, release of greenhouse gases, and mineral and water waste. Conversely, the method S100 implements direct capture of a gaseous carbon dioxide mixture from the air and transforms this mixture into a hydrocarbon precursor for diamond production. For example, Blocks of the method S100 can be executed to: capture the gaseous carbon dioxide mixture directly from ambient air (e.g., anywhere in the world); transform this gaseous carbon dioxide mixture into a hydrocarbon precursor; and then transform this hydrocarbon precursor into diamonds, thereby both removing airborne carbon dioxide waste and generating a valuable secondary product from excess carbon dioxide in ambient air.

Further, by implementing direct air capture, the method S100 can extract carbon dioxide from air captured in a particular location or place of significance (e.g., to the diamond owner) such that diamonds generated from this carbon dioxide can be linked to the particular location or place. For example, a mobile carbon capture device can be deployed to a particular location—such as a person's favorite vacation city, hometown, marriage proposal site, or honeymoon site or to a location of a sporting event, political rally, or company event—to extract carbon dioxide from air captured in this particular location according to Blocks of the method S100. This carbon dioxide can then be further processed according to subsequent Blocks of the method S100 described below to generate a diamond from this carbon dioxide.

In particular, once captured from the air, the low-purity gaseous carbon dioxide mixture can be purified via liquefaction to generate a high-purity liquid carbon dioxide mixture which can be further purified and/or filtered in order to achieve a threshold carbon dioxide concentration. Once the high-purity liquid carbon dioxide mixture reaches the threshold carbon dioxide concentration, this high-purity liquid mixture can be converted to a high-purity gaseous carbon dioxide mixture which can then be reacted with hydrogen gas and/or other inert gases in a reactor, at specific temperatures, and under particular conditions according to the method in order to enable and control methanation of the gaseous carbon dioxide mixture to form a gaseous hydrocarbon mixture (or "hydrocarbon precursor"). This hydrocarbon precursor can serve as an input to the diamond reactor or can be further purified prior to generating a higher-purity hydrocarbon precursor in order to decrease the concentration of impurities present in the diamond reactor.

In one variation, to further prepare this initial hydrocarbon precursor for the reaction in the diamond reactor, the initial hydrocarbon mixture can be further purified to generate a higher-purity hydrocarbon precursor exhibiting a concentration of methane above a threshold concentration of methane (e.g., greater than 96.0 percent methane, greater than 99.95 percent methane, greater than 99.9995 percent). For example, the gaseous hydrocarbon mixture can be liquefied and run through an absorption cartridge to remove Nitrogen and other impurities from the mixture, and thus achieve the hydrocarbon precursor with a concentration of methane above a threshold concentration of methane and an impurity (e.g., Nitrogen) concentration below a threshold impurity concentration.

Once these threshold concentrations are met, the hydrocarbon precursor reacts under particular temperature and pressure conditions (e.g., high temperatures) in the diamond reactor (e.g., chemical vapor deposition reactor) to generate diamond crystals. In one example, 10 kg of carbon dioxide captured from the air can be further processed according to the method S100 to generate approximately 80 carats of finished diamond.

A diamond thus produced according to the method S100 can then be linked to the particular location, event, date, and/or people present near the mobile carbon capture device when its originating carbon dioxide was captured. For example: a diamond can be engraved with a unique serial number; a file specifying a geospatial location, a date, a description of a nearby event, and/or a list of people present can be generated and stored in a database; and this file can be linked to the unique serial number of this diamond, as shown in FIG. 3.

Therefore, the method S100 can be executed to generate diamonds from carbon dioxide extracted directly from the atmosphere, thus benefiting the environment by reducing carbon dioxide in the atmosphere and providing an alternative to natural diamonds sourced via dangerous and environmentally-unfriendly practices. Furthermore, because these diamonds are generated from carbon dioxide extracted from air captured in a particular location, at a particular date and time, and/or near a particular individual or group of people, these diamonds: can be uniquely associated with particular locations, times, dates, and people and therefore with individual stories; and can thus achieve greater relevance and importance to owners and wearers (e.g., than mined diamonds).

3. "Clean" Diamond Production

The method S100 can be executed to generate "lab-grown" diamonds from carbon captured from the air. By extracting carbon from atmospheric carbon dioxide captured from air, the method S100 enables diamond production via a carbon negative process. Additionally, the initial capture of carbon dioxide from the atmosphere may negate or offset all carbon emissions or a portion of carbon emissions generated during chemical processes that occur during execution of the method S100, thus enabling a carbon-neutral or carbon-negative process.

Further, the method S100 can be executed via power harvested from a renewable power source. For example, the method includes reacting the hydrocarbon precursor via chemical vapor deposition to generate a diamond crystal. As shown in FIG. 2, the electricity required to power the chemical vapor deposition reaction in Block S150 can be harvested from a sustainable power source, such as wind, solar, or geothermal. In one example, power is harvested from landfill gas. In another example, power is harvested from biogas (e.g., from farm waste). Additionally, power can be recycled within this process, such as by collecting a portion of the low-purity and/or high-purity hydrocarbon precursor mixtures to power a set of power generators. Power produced by these power generators—in combination with power generated by the sustainable power source (e.g., wind power source)—can be harvested to power the diamond reactor. Further, any excess power produced by the power generators or the sustainable power source can be returned to the power grid and recycled for future power harvesting.

Similarly, the method S100 can implement a closed-loop process that generates no water waste and recycles steam and cooling water within the closed-loop process.

4. Air Capture

Block S110 of the method S100 recites ingesting a first mixture (e.g., a low-purity carbon dioxide mixture) extracted from a first air sample (e.g., via amine filtration), the first mixture including carbon dioxide and a first concentration of impurities including nitrogen. In one variation, Block S110 of the method recites: extracting a gaseous mixture of carbon dioxide and impurities from an air source (e.g., via amine filtration), the gaseous mixture exhibiting a first concentration of carbon dioxide and a first concentration of impurities. The resulting gaseous mixture (i.e., the first mixture) is a low-purity gaseous mixture of carbon dioxide (e.g., less than 80.0 percent carbon dioxide). This low-purity carbon dioxide mixture also includes concentrations of impurities found in air such as Nitrogen, Argon, and other gases.

In one implementation, the low purity, gaseous carbon dioxide mixture is extracted from atmospheric air via amine filtration. In particular, in this implementation, an air sample, including a first concentration of carbon dioxide, can be collected during an air capture period. An amount of carbon dioxide can then be extracted from the first air sample via filtration (e.g., amine filtration). This amount of carbon dioxide can then be heated, in a chamber, to generate a carbon dioxide mixture including a second concentration of carbon dioxide greater than the first concentration of carbon dioxide. This carbon dioxide mixture can then be stored in a container for further processing (e.g., at a second location). For example, air can be drawn into a reservoir (e.g., within a carbon capture device) defining an opening through which air enters the reservoir. The reservoir can include a filter arranged within the opening and configured to collect carbon dioxide molecules in the air flowing through the opening while enabling other particles in the air to flow through freely. Once the filter is saturated with carbon dioxide, the filter can be heated (e.g., to temperatures between 95 degrees Celsius and 120 degrees Celsius) to extract carbon dioxide gas from the filter. Upon heating the filter, the gaseous carbon dioxide mixture is released from the filter. This gaseous carbon dioxide mixture can then be collected and stored (e.g., in a container). Later, the gaseous carbon dioxide mixture (e.g., stored in the container) can be ingested for further processing.

In one implementation, direct air capture via amine filtration results in a low-purity gaseous carbon dioxide mixture exhibiting a carbon dioxide concentration between seventy percent and eighty-five percent. The low-purity gaseous carbon dioxide mixture exhibits an impurity concentration between fifteen percent and thirty percent, the impurity concentration including a concentration of Nitrogen (e.g., in the form of NX compounds such as Nitrogen oxides and/or ammonia). Nitrogen, however, can be toxic to diamond crystal growth if present in the diamond reactor. Therefore, this initial low purity gaseous carbon dioxide mixture can be further treated to increase the concentration of carbon dioxide and reduce the concentration of impurities in the mixture. In particular, the low purity gaseous carbon dioxide mixture can be purified via a liquefaction technique to reduce the concentration of Nitrogen (e.g., in NX compounds) in the carbon dioxide mixture.

In one implementation, a mobile carbon capture device can be deployed to various locations to capture this gaseous carbon dioxide mixture from atmospheric air. The mobile carbon capture device can include a filtering device for extracting the low-purity carbon dioxide mixture and tanks for storing the carbon dioxide mixture. For example, the mobile carbon capture device can be deployed to a particular region and extract carbon dioxide at a target rate (e.g., 10 kg/day, 100 kg/day, 1000 kg/day). Therefore, the mobile carbon capture device can both capture air and filter the air to separate and store the low-purity carbon dioxide mixture.

In another implementation, the carbon capture device is located in a fixed location. In one example, the carbon capture device can be mounted to a building or structure (e.g., a laboratory, a power plant). The fixed carbon capture device can collect and store low purity gaseous carbon dioxide, which may be retrieved for further processing according to the method S100.

5. Carbon Dioxide Purification

Block S120 of the method S100 recites: conveying the first mixture (e.g., the low-purity carbon dioxide mixture) through a pressurized unit (e.g., a liquefaction unit) at temperatures within a first temperature range to promote liquefaction of the first mixture to generate a first exhaust stream of impurities including nitrogen and a second mixture (e.g., a high-purity carbon dioxide mixture) including carbon dioxide and a second concentration of impurities less than the first concentration of impurities in the first mixture.

In one variation, Block S120 of the method S100 recites: condensing the gaseous carbon dioxide mixture (e.g., the low-purity carbon dioxide mixture) via liquefaction to generate a liquid mixture of carbon dioxide and impurities, the liquid mixture exhibiting a second concentration of carbon dioxide greater than the first concentration of carbon dioxide and a second concentration of impurities less than the first concentration of impurities. In this step, the low purity gaseous carbon dioxide mixture is liquefied at low temperatures and with an applied pressure to generate a higher purity liquid mixture. The resulting higher purity liquid mixture of carbon dioxide exhibits a greater concentration of carbon dioxide and lower concentration of impurities (e.g., Nitrogen) than the input gaseous carbon dioxide mixture.

The liquefaction process includes subjecting the low purity carbon dioxide mixture (e.g., within a storage Dewar) to temperatures below the critical temperature of carbon dioxide (e.g., less than 31 degrees Celsius) and at pressures below the critical pressure of carbon dioxide (e.g., less than 73 bar). In one implementation, the low purity gaseous carbon dioxide mixture is transferred to a cryogenic storage Dewar (e.g., with capacity between 50 L and 100 L) and held at a temperature of approximately −20 degrees Celsius (±1 degree Celsius) and a pressure of approximately 20 Bar (±1 Bar). Under these conditions, the low purity gaseous carbon dioxide mixture can be liquefied and collected for further processing, while other gases (e.g., Hydrogen, Nitrogen) present in the mixture do not liquefy and are reduced.

Once liquefaction of the low-purity gaseous carbon dioxide mixture is complete, the resulting liquid carbon dioxide mixture exhibits a higher concentration of carbon dioxide than the initial low purity gaseous carbon dioxide mixture. In one implementation, the liquid mixture exhibits a carbon dioxide concentration greater than 95.0 percent and a concentration of impurities (e.g., Hydrogen, trace amounts of Nitrogen) less than five percent. For example, a low purity gaseous carbon dioxide mixture exhibiting a first concentration of carbon dioxide of 70 percent and a first concentration of impurities of 30 percent can be liquefied in a storage Dewar to generate a high purity liquid carbon dioxide mixture exhibiting a second concentration of carbon dioxide between 98 percent and 99.5 percent and a second concentration of impurities between 0.5 percent and 2 percent.

The liquid carbon dioxide mixture can then be converted to a second gaseous carbon dioxide mixture (e.g., a high purity gaseous carbon dioxide mixture) via an expander in Block S122. Thus, the high purity liquid carbon dioxide mixture is converted back to a gaseous state in preparation for methanation of the second gaseous carbon dioxide mixture.

In one variation, the method S100 includes Block S124 which recites cleaning the second gaseous carbon dioxide mixture via absorption to decrease the second concentration of impurities and increase the second concentration of carbon dioxide exhibited by the second gaseous carbon dioxide mixture. In this variation, the second gaseous carbon dioxide mixture is further purified after liquefaction and expansion via an absorption process which further removes impurities (e.g., Nitrogen oxides, ammonia) present in the second gaseous carbon dioxide mixture. The second gaseous carbon dioxide mixture can be run through an absorption cartridge including a filter configured to react with impurities present in the second gaseous carbon dioxide mixture and thus extract these impurities from the second gaseous carbon dioxide mixture. For example, the second gaseous carbon dioxide mixture can be run through an absorption cartridge at a flow rate between 8 Liters/minute and 12 Liters/minute. Upon exiting the absorption cartridge, the second gaseous carbon dioxide mixture can exhibit a Nitrogen concentration in the parts-per-trillion (PPT) levels.

6. Hydrocarbon Precursor Synthesis

Block S130 of the method S100 recites: in a methanation reactor, mixing the second mixture (e.g., a high-purity carbon dioxide mixture, a high purity gaseous carbon dioxide mixture) with a stream of hydrogen to generate a first hydrocarbon mixture (i.e., a hydrocarbon precursor) including hydrocarbons (e.g., methane) and a third concentration of impurities including nitrogen, carbon dioxide, and hydrogen. In one variation, Block S130 recites: in a first reactor, exposing the second gaseous mixture to a stream of hydrogen, in the presence of a catalyst, to generate a hydrocarbon precursor via methanation of the second gaseous mixture, the hydrocarbon precursor exhibiting a first concentration of methane, a third concentration of carbon dioxide and a third concentration of impurities.

Upon completion of the liquefaction, expansion and purification steps described above, the second gaseous carbon dioxide mixture (or "high purity gaseous carbon dioxide mixture") exhibits a carbon dioxide concentration (e.g., greater than 95 percent) and an impurity concentration (e.g., less than 5 percent) sufficient for the methanation reaction to occur. In particular, after liquefaction and before methanation, the high-purity gaseous carbon dioxide mixture can exhibit an NX (e.g., NO, $NH_3$) concentration less than 2 parts-per-billion (e.g., 1.2 parts-per-billion). For example, upon reaching a carbon dioxide concentration at or above a threshold carbon dioxide concentration (e.g., at or above 95.0 percent carbon dioxide) and reducing a concentration of Nitrogen to below a maximum Nitrogen concentration (e.g., below 2 parts-per-billion), the high-purity gaseous carbon dioxide mixture can be treated with a stream of Hydrogen gas and/or other reactants at particular flowrates, temperatures, and pressures in a reactor configured for catalytic methanation, such that the high-purity gaseous carbon dioxide mixture is converted to a hydrocarbon mixture including methane.

In one implementation, the high-purity gaseous carbon dioxide mixture (e.g., greater than 95 percent carbon dioxide concentration) is transferred to a methanation reactor configured to promote a catalytic methanation reaction. This methanation reactor system (e.g., the reactor and the high-purity gaseous carbon dioxide mixture) can be pressurized by introducing a stream of Hydrogen gas to the system, which triggers methanation of the high-purity gaseous carbon dioxide mixture. In particular, in this implementation, the high-purity gaseous carbon dioxide mixture can be treated (e.g., mixed) with a stream of hydrogen (e.g., a stream of hydrogen gas), in the methanation reactor, in the presence of a catalyst, to generate a hydrocarbon precursor via methanation of the high-purity gaseous carbon dioxide mixture. The hydrocarbon precursor can include methane and impurities such as hydrogen, carbon dioxide, and/or Nitrogen (e.g., less than 350 parts-per-million, less than 10 parts-per-million, less than 2 parts-per-billion).

For example, upon exiting the methanation reactor, the resulting hydrocarbon precursor (or "initial hydrocarbon mixture") can exhibit: a concentration of hydrocarbons (e.g., a concentration of methane greater than 96 percent); and a concentration of impurities including a concentration of carbon dioxide (e.g., less than 1 percent), a concentration of hydrogen (e.g., less than 2 percent), and a concentration of Nitrogen (e.g., less than 350 parts-per-million, less than 10 parts-per-million, less than ten parts-per-billion). In one example, upon exiting the methanation reactor, the resulting hydrocarbon precursor can exhibit a concentration of Nitrogen (e.g., N2) less than 350 parts-per-million. In another example, upon exiting the methanation reactor, the resulting hydrocarbon precursor can exhibit a concentration of impurities (e.g., including Hydrogen, Carbon Dioxide, Argon, and/or Nitrogen) less than a threshold concentration of impurities (e.g., less than 0.0005 percent) including a concentration of Nitrogen less than a threshold concentration of Nitrogen (e.g., less than 1.2 parts-per-billion), such that the hydrocarbon precursor exhibits a methane carbon concentration exceeding a threshold concentration of methane (e.g., greater than 99.9995 percent).

In this implementation, hydrogen gas can be pumped into the methanation reactor to react with the high-purity gaseous carbon dioxide mixture (e.g., in the presence of a catalyst) to generate the hydrocarbon precursor. In one example, an electrolyzer tank can be coupled to the methanation reactor. The electrolyzer tank can be configured to convert water stored in the electrolyzer tank into hydrogen gas and oxygen, and this resulting hydrogen gas can be pumped into the methanation reactor.

In order to generate a hydrocarbon precursor exhibiting a threshold concentration of methane (e.g., greater than 95 percent methane) and minimal concentration of impurities (e.g., Nitrogen concentration measured at parts-per-billion), the introduction of Nitrogen and other impurities during methanation in the reactor can be minimized. In one implementation, a stream of an inert gas (e.g., Argon) is cycled through the methanation reactor to purge the methanation reactor of impurities. For example, a stream of Argon can be cycled through the methanation reactor prior to introduction of the high-purity gaseous carbon dioxide mixture into the methanation reactor. Further, in the example, the stream of Argon can be cycled through the methanation reactor both during methanation of the high-purity gaseous carbon dioxide mixture (e.g., while the high-purity gaseous carbon dioxide mixture is present in the methanation reactor) and after the high-purity gaseous carbon dioxide mixture exits the methanation reactor to purge impurities from within the methanation reactor and to maintain an operational pressure within the methanation reactor. In this example, the resulting hydrocarbon precursor (i.e., the first hydrocarbon mixture) can exhibit: a concentration of hydrocarbons (e.g., a concentration of methane); and a concentration of impurities including carbon dioxide, Hydrogen, Argon, and/or Nitrogen.

In one implementation, the high-purity gaseous carbon dioxide mixture can be transferred to the methanation reactor, treated with a stream of Hydrogen gas, in the presence of a catalyst, to pressurize the high-purity gaseous carbon dioxide mixture in the methanation reactor, and treated with a stream of Argon gas to prevent introduction of Nitrogen to the reactor. Under these conditions, the high-purity gaseous carbon dioxide mixture can undergo methanation and generate a hydrocarbon precursor exhibiting a concentration of methane greater than 97 percent and a concentration of impurities less than 3 percent. For example, a stream of Argon can be introduced to the methanation reactor system such that the resulting hydrocarbon precursor output from the reaction exhibits a concentration of impurities less than 3 percent, the concentration of impurities including a Nitrogen concentration less than a threshold concentration of Nitrogen (e.g., less than 350 parts-per-million, less than 10 parts-per-million, less than 1.2 parts-per-billion).

In one implementation, this hydrocarbon precursor, exhibiting a concentration of methane greater than 97 percent, serves as the hydrocarbon precursor which undergoes the CVD reaction to generate diamonds in the diamond reactor. Alternatively, as described below, this hydrocarbon precursor (or "initial hydrocarbon precursor") can undergo further purification and preparation to generate a more highly-purified hydrocarbon precursor.

6.1 Variation: Nitrogen Purge

In one variation, the hydrocarbon precursor can be transferred from the methanation reactor into an accumulator configured to estimate a concentration of nitrogen present in the hydrocarbon precursor in Block S132. In this variation, in response to detecting a concentration of nitrogen exceeding a threshold concentration, the hydrocarbon precursor can be diverted to a secondary vessel for further processing. Alternatively, in response to detecting the concentration of nitrogen below the threshold concentration, the hydrocarbon precursor can be conveyed through the separation unit.

In one implementation, the hydrocarbon precursor can be purified in the buffer vessel, such that the hydrocarbon precursor can be recovered. For example, the hydrocarbon precursor can be transferred from an outlet of the methanation reactor into the accumulator. The accumulator can include an inline nitrogen reader configured to estimate a concentration of nitrogen present in the hydrocarbon precursor. Then, in response to the concentration of nitrogen exceeding a threshold concentration (e.g., greater than 400 parts-per-million, greater than 10 parts-per-million, greater than 1.2 parts-per-billion), the hydrocarbon precursor can be diverted (e.g., via a purge line) into a buffer vessel. In this example, the hydrocarbon precursor can be conveyed through a secondary separation unit (e.g., a set of filters) configured to remove nitrogen from the hydrocarbon precursor. The hydrocarbon precursor can then be deposited in the buffer vessel including a second inline nitrogen reader installed at an inlet of the buffer vessel and configured to measure the concentration of nitrogen in the hydrocarbon precursor. Then, in response to detecting the concentration of nitrogen below the threshold concentration, the hydrocarbon precursor can be transferred from an outlet of the buffer vessel to an inlet of the separation unit (e.g., filters, liquefaction unit). Alternatively, the hydrocarbon precursor can be transferred back to the accumulator for further analysis.

Alternatively, in another implementation, at the accumulator, in response to the concentration of nitrogen exceeding the threshold concentration of nitrogen in the hydrocarbon precursor, the hydrocarbon precursor can be diverted to flare.

7. Hydrocarbon Precursor Purification

Block S140 of the method S100 recites: conveying the first hydrocarbon mixture (e.g., from an outlet of the methanation reactor) through a separation unit configured to remove impurities from the hydrocarbon mixture to generate a second hydrocarbon mixture including hydrocarbons and a fourth concentration of impurities less than the third concentration of impurities.

The hydrocarbon precursor can be further processed to increase a concentration of methane and decrease a concentration of impurities in the mixture. In particular, the hydrocarbon precursor can be transferred from an outlet of the methanation unit through a separation unit (e.g., a set of filters, a liquefaction unit) configured to reduce a concentration of impurities in the hydrocarbon precursor.

In one implementation, the hydrocarbon precursor can be passed through a set of filters (e.g., a filter membrane) at an outlet of the methanation reactor. The set of filters can be configured to collect impurities—such as compounds containing Nitrogen (e.g., nitric oxide, nitrogen dioxide), hydrogen, carbon dioxide, argon, or other gases (e.g., other than methane)—present in the hydrocarbon mixture. For example, the hydrocarbon precursor can exhibit an initial concentration of impurities prior to exiting the outlet of the methanation reactor. As the hydrocarbon precursor flows through the outlet of the methanation reactor, the hydrocarbon precursor can also flow through a filter membrane integrated into the outlet. Upon exiting the outlet and the filter membrane, the hydrocarbon mixture can exhibit an exit concentration of impurities (e.g., less than five percent) less than the initial concentration of impurities. The filter membrane—including impurities extracted from the hydrocarbon mixture—can then be cleaned or replaced prior to a next cycle or in response to an amount (e.g., quantity, concentration) of impurities in the filter membrane exceeding a threshold amount (e.g., a threshold quantity, a threshold concentration). In one example, the hydrocarbon precursor can exhibit a concentration of impurities less than five percent after passing through the set of filters, such that a concentration of hydrocarbons (e.g., methane) exceeds ninety-five percent. In another example, the hydrocarbon precursor can exhibit a concentration of impurities less than three percent after passing through the set of filters, such that a concentration of hydrocarbons (e.g., methane) exceeds ninety-seven percent.

Alternatively, in another implementation, the method S100 includes condensing the initial hydrocarbon precursor via liquefaction to generate a liquid hydrocarbon mixture exhibiting a second concentration of methane greater than the first concentration of methane and a fourth concentration of impurities less than the third concentration of impurities. Thus, the gaseous hydrocarbon mixture can be liquefied to further purify the mixture before it is run through the CVD reactor.

In this implementation, upon exiting the methanation reactor, the initial hydrocarbon precursor (e.g., a gaseous hydrocarbon mixture) exhibits a high concentration of methane. After liquefaction of the initial hydrocarbon precursor, the resulting liquid hydrocarbon mixture can exhibit a higher concentration of methane by reducing all non-hydrocarbon gases in this mixture (e.g., nitrogen, carbon dioxide, hydrogen, argon). For example, the initial hydrocarbon precursor can exhibit a concentration of methane greater than 97 percent. This initial hydrocarbon precursor can undergo liquefaction including pressurizing the gaseous carbon dioxide mixture and cooling the mixture to a temperature below its critical temperature. Once liquefaction of the initial hydrocarbon precursor is complete, the resulting liquid hydrocarbon mixture can exhibit a concentration of methane greater than 99 percent (e.g., 99.9 percent). For example, after liquefaction, the liquid hydrocarbon mixture can exhibit a concentration of hydrocarbons (e.g., methane) exceeding of 99.5 percent and the concentration of impurities can be reduced to less than 0.5 percent, including a concentration of Argon gas between 0.01 percent and 0.10 percent. In another example, after liquefaction, the liquid hydrocarbon mixture can exhibit a concentration of methane greater than 99.9 percent and the Argon gas present in the mixture can be reduced to a concentration between 0.01 percent and 0.10 percent. Similarly, NX (e.g., NO, $NH_3$) gas present in the mixture can be reduced even further to a concentration less than 1.2 parts-per-billion.

In this implementation, the resulting liquid hydrocarbon mixture can then be converted to a gaseous hydrocarbon mixture in Block S142, the gaseous hydrocarbon exhibiting lower concentrations of impurities than the initial hydrocarbon precursor.

Figure 5A:
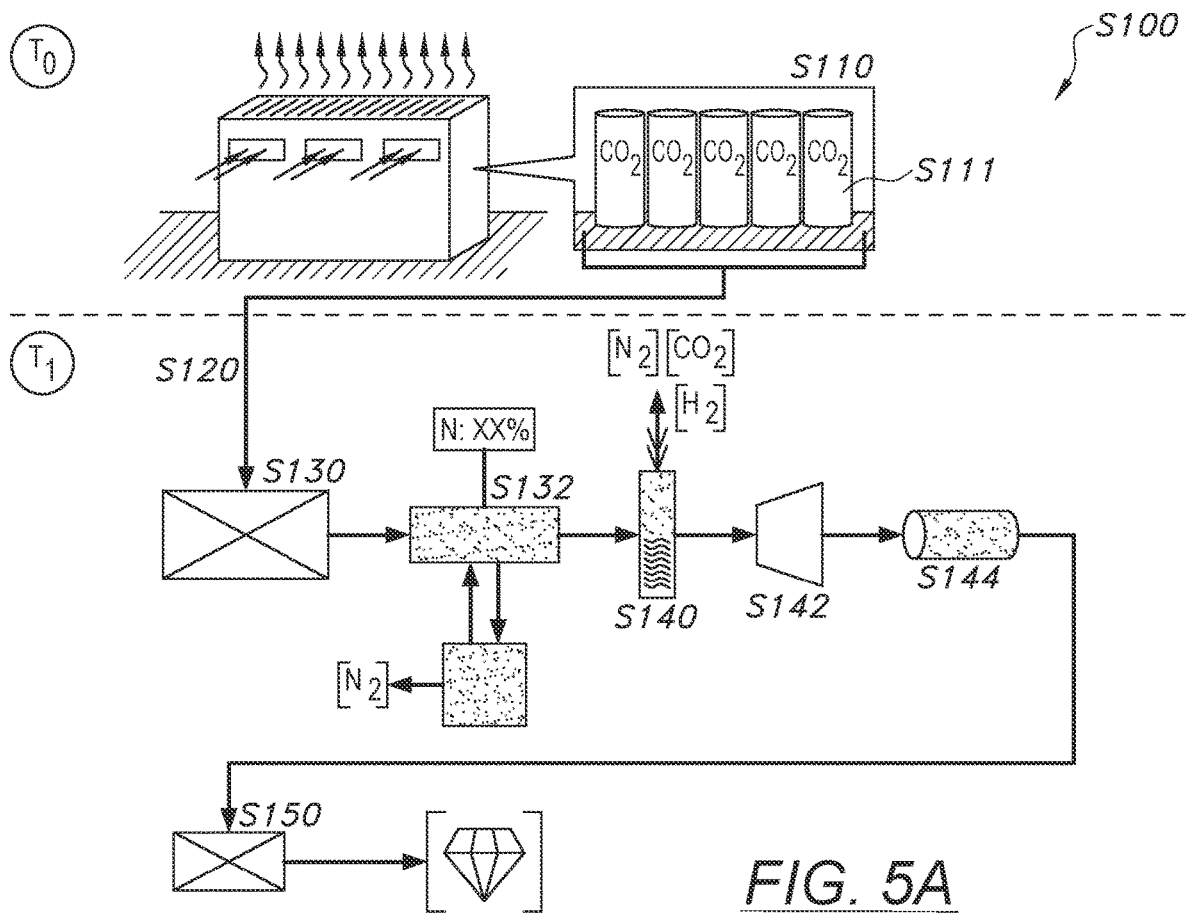
FIGS. 5A and 5B are flowchart representations of one variation of the method.
Figure 5B:
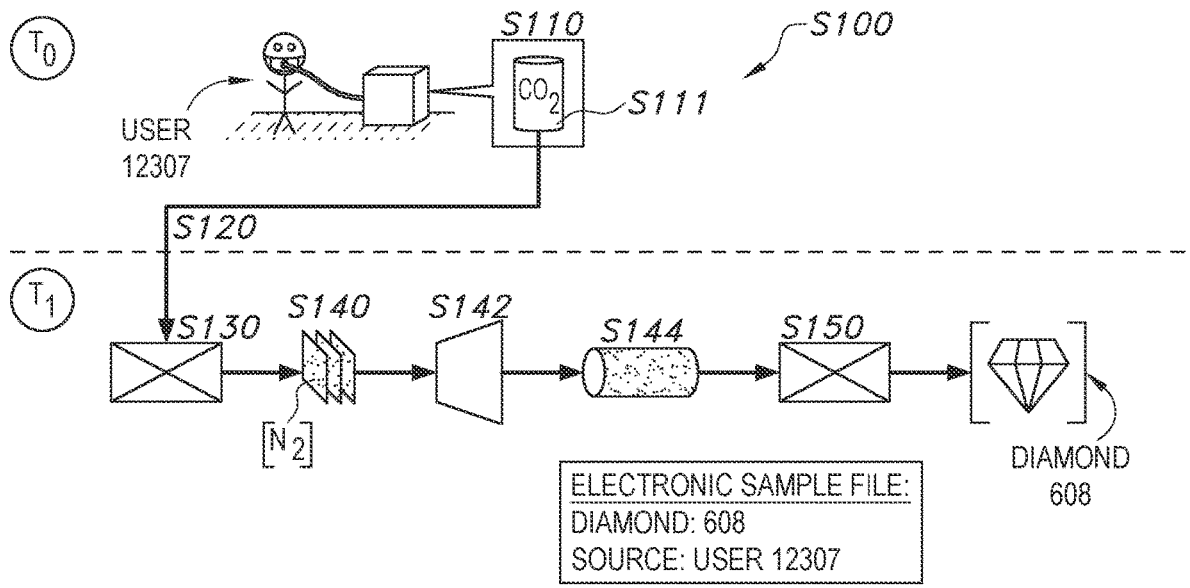

In one implementation, as shown in FIGS. 5A and 5B, the initial hydrocarbon precursor can be purified according to a particular method based on a volume of the initial hydrocarbon precursor. In particular, in this implementation, in response to a volume of the initial hydrocarbon precursor falling below a threshold volume, the initial hydrocarbon precursor can be conveyed through a liquefaction unit configured to remove impurities from the hydrocarbon precursor via liquefaction to generate: an exhaust stream including impurities (e.g., carbon dioxide, hydrogen, nitrogen); and a final hydrocarbon precursor exhibiting a second concentration of impurities less than a first concentration of impurities of the initial hydrocarbon precursor. Alternatively, in response to the volume of the initial hydrocarbon precursor exceeding the threshold volume, the initial hydrocarbon precursor can be conveyed through a set of filters (e.g., a membrane filter) configured to collect impurities present in the initial hydrocarbon precursor to generate the final hydrocarbon precursor.

For example, a high volume of carbon dioxide collected by a first carbon capture device semi-permanently deployed at a first target location can be processed according to Blocks of the method S100 to generate a high volume of methane gas (i.e., the hydrocarbon precursor). This high volume of methane gas can be purified via a liquefaction unit configured to: continuously (e.g., semi-continuously) ingest high volumes of methane gas—exhibiting an initial concentration of impurities—generated from carbon dioxide collected at the first target location by the carbon capture device; and continuously (e.g., semi-continuously) output an exhaust stream of impurities and high volumes of methane gas exhibiting a final concentration of impurities less than the initial concentration of impurities.

Additionally and/or alternatively, in another example, a low volume of carbon dioxide collected by a second carbon capture device transiently deployed to a second target location for a particular event (e.g., a sporting event, a wedding, a fundraiser) of a fixed duration can be processed according to Blocks of the method S100 to generate a low volume of methane gas. This low volume of carbon dioxide and resulting low volume of methane gas can be processed in a singular, batch process such that the low volume of carbon dioxide remains isolated from other volumes of carbon dioxide not collected from the second target location and during the particular event. This low volume of methane gas can then be purified via a set of filters (e.g., a membrane filter) configured to: ingest a low volume of methane gas exhibiting an initial concentration of impurities—generated from carbon dioxide collected at the second target location by the second carbon capture device; collect impurities (e.g., hydrogen, carbon dioxide, nitrogen) present in the low volume of methane gas; and output methane gas exhibiting a final concentration of impurities less than the initial concentration of impurities.

8. Additional Purification of the Hydrocarbon Precursor

In one variation, the second hydrocarbon mixture can be transferred from the separation unit and conveyed through a compressor to further reduce all non-hydrocarbon gases present in the second hydrocarbon mixture in Block S144. Additionally and/or alternatively, in another variation, the second hydrocarbon mixture can then be further purified via absorption to generate a highly-purified hydrocarbon precursor (or "final hydrocarbon precursor") in Block S146.

Block S144 recites purifying the gaseous hydrocarbon mixture via absorption to generate a hydrocarbon precursor exhibiting a third concentration of methane (e.g., after purification via absorption) greater than the second concentration of methane (e.g., prior to purification via absorption) and a fifth concentration of impurities (e.g., after purification via absorption) less than the fourth concentration of impurities (prior to purification via absorption). Thus, before running the mixture through the diamond reactor (e.g., the CVD reactor), the method S100 can implement a fuel polishing step to further purify and prepare the gaseous hydrocarbon mixture for the CVD reactor.

For example, the second hydrocarbon mixture can be run through an absorption cartridge at a flowrate approximately between 2.0 Liters/minute and 3.0 Liters/minute in order to remove NX (e.g., NO, $NH_3$) and other impurities from the mixture. The absorption cartridge can include a filter configured to react with impurities in the gaseous hydrocarbon mixture, such that these impurities cling to the filter while the remainder of the gaseous hydrocarbon mixture passes through the filter.

Therefore, in this variation, the initial hydrocarbon precursor generated via methanation of the carbon dioxide mixture can be purified via filters, liquefaction, drying, compression, adsorption, and/or any combination of these techniques to generate a higher-purity hydrocarbon precursor (or "hydrocarbon precursor"). The hydrocarbon precursor can exhibit a sufficiently high concentration of methane (e.g., greater than 97 percent) and thus a sufficiently low concentration of impurities (e.g., less than 3 percent) such that, when deposited in the diamond reactor, diamonds may readily grow according to a set rate and exhibiting sufficient quality (e.g., clarity, cut, color, carat weight). In one example, this higher-purity hydrocarbon precursor (i.e., second hydrocarbon mixture) can exhibit a concentration of methane greater than a threshold concentration of methane (e.g., greater than 99.9995 percent methane). Additionally and/or alternatively, in another example, the higher-purity hydrocarbon precursor can exhibit a concentration of impurities including a concentration of nitrogen less than 10 parts-per-billion (e.g., 2 parts-per-billion, 6 parts-per-billion, 9 parts-per-billion).

9. Diamond Reactor

Block S150 of the method S100 recites: depositing the second hydrocarbon mixture in a diamond reactor containing a set of diamond seeds to generate a first set of diamonds via chemical vapor deposition. In one variation, Block S150 of the method S100 recites, in a diamond reactor at a set temperature, exposing the hydrocarbon precursor to a diamond seed to generate a diamond crystal via chemical vapor deposition (or "CVD").

The high-purity hydrocarbon precursor can flow into a CVD reactor (e.g., a vacuum chamber) configured to generate diamond crystals via chemical vapor deposition.

For example, a diamond seed can be placed in the CVD reactor. As the hydrocarbon precursor flows into the CVD reactor, the CVD reactor can be heated to very high temperatures (e.g., greater than 800 degrees Celsius). Heating the CVD reactor to these high temperatures causes carbon ions to dispel from hydrocarbon precursor. These carbon ions may layer into the diamond seed, and the diamond seed can grow into a diamond (e.g., a rough diamond configured to be cut into one or more gemstones).

The CVD reactor requires electricity to generate enough heat for the reaction to occur. In one implementation, a power generator supplies electricity to the CVD reactor. For example, methane fuels extracted from the gaseous hydrocarbon mixture and/or hydrocarbon precursor can be recycled to the power generator, which in turn can supply electricity to the CVD reactor. Additionally and/or alternatively, landfill gas can be collected and supplied to the power generator to generate electricity. In another implementation, a sustainable power source (e.g., solar panels, a wind turbine) supplies power to the CVD reactor. Further, a sustainable power source can be implemented in combination with a power generator to power the CVD reactor. Once the CVD reaction is complete, excess unused power can be returned to the grid for future use.

In one implementation, the high-purity hydrocarbon precursor enters the CVD reactor exhibiting a concentration of methane between 96.0 percent and 99.9999 percent. The CVD reactor can be tuned accordingly based on the concentration of methane and the concentration of impurities (e.g., Hydrogen gas, carbon dioxide, Argon, Nitrogen) of the hydrocarbon precursor. For example, the temperature and pressure in the CVD reactor can be adjusted based on the concentration of methane in the hydrocarbon precursor.

Air present in the gaseous hydrocarbon mixture and CVD reactor can be purged from the CVD reactor to increase efficiency and yield of the reaction. In one implementation, air is purged from the CVD reactor by cycling an inert blend through the CVD reactor. For example, a stream of Hydrogen gas can be cycled through the CVD reactor at set intervals throughout the chemical vapor deposition process. Similarly, a stream of an inert gas (e.g., Argon) can be cycled through the CVD reactor to act as a carrier and therefore improve a rate of the reaction and a rate of diamond growth.

The CVD reactor can be configured to grow diamonds from a hydrocarbon precursor exhibiting a particular concentration of methane (e.g., methane). Therefore, the flowrate of the hydrocarbon precursor into the CVD reactor can be adjusted to control a concentration of methane present in the CVD reactor. For example, if the hydrocarbon precursor exhibits a concentration of methane of 99.9 percent, the flowrate of the hydrocarbon precursor going into the CVD reactor can be lowered. However, if the hydrocarbon precursor exhibits a concentration of methane of 97 percent, then the flowrate of the hydrocarbon precursor going into the CVD reactor can be increased.

In one variation, a stream of Hydrogen gas is cycled through the CVD reactor at a set flowrate based on the concentration of Hydrogen gas in the hydrocarbon precursor. For example, if the hydrocarbon precursor exhibits a concentration of methane of 99.99 percent and thus a concentration of impurities—including Hydrogen gas and carbon dioxide—of 0.01 percent, a stream of Hydrogen gas can be cycled through the CVD reactor a first flowrate based on the relatively low concentration of Hydrogen gas present in the hydrocarbon precursor (and the CVD reactor). However, if the hydrocarbon precursor exhibits a concentration of methane of 97 percent and thus a concentration of impurities below 3 percent, a stream of Hydrogen gas can be cycled through the CVD reactor at a second flowrate less than the first flowrate based on the relatively high concentration of Hydrogen gas already present in the hydrocarbon precursor (and the CVD reactor).

The grow rate of the diamonds in the CVD reactor can be adjusted based on: the concentration of methane in the hydrocarbon precursor entering the CVD reactor; the flow rate of the hydrocarbon precursor can be adjusted to alter the grow rate of the diamonds; and/or the temperature within the CVD reactor In one implementation, the method S100 can be executed to generate approximately 80 rough carats of diamond from an initial air capture of 10 kg of carbon dioxide.

10. Variation: HP-HT Diamonds

In one variation, diamonds can be generated via a High-Pressure-High-Temperature (or "HP-HT) process. In this variation, an HP-HT reactor can replace the CVD reactor in Block S150 of the method S100.

In this variation, high-purity carbon black or graphite can serve as the input to the HP-HT reactor, rather than the hydrocarbon precursor. The hydrocarbon precursor can be generated according to the methods described above and processed further to generate carbon black or graphite.

For example, the high-purity carbon dioxide mixture can react to generate the hydrocarbon precursor (e.g., a high-purity gaseous hydrocarbon mixture) via methanation in Block S130. Graphite can be extracted from the hydrocarbon precursor by heating this mixture in a contained chamber absent oxygen (e.g., via pyrolysis or electrolysis) and in the presence of a catalyst configured to promote this reaction (e.g., an iron-oxide catalyst). Once graphite has been extracted from the hydrocarbon precursor, the graphite can be deposited in the HP-HT reactor. A diamond seed can be deposited in the graphite which can then be exposed to high temperatures and pressures in the HP-HT reactor. Conditions (e.g., temperature, pressure) within the HP-HT reactor can be set such that the graphite material transforms under these conditions and thus begins to form a diamond around the diamond seed.

11. Location-Based Air Capture

In one implementation, carbon extracted from air via direct air capture can be sourced from particular regions or locations via a mobile carbon capture device. This mobile carbon capture device can be configured to extract the low-purity carbon dioxide mixture from air via amine filtration and to store this mixture for further processing elsewhere (e.g., in a laboratory).

In one variation, the low-purity carbon dioxide mixture can be extracted from air from a particular location or place of significance (e.g., to the diamond owner) such that diamonds generated from carbon captured from this air can be linked to the particular location. For example, a couple may purchase an engagement ring with a diamond generated from carbon that is sourced from air in a location of significance to the couple (e.g., a place where the couple met, a place where the couple vacationed).

In another example, players on a championship football team may receive rings with diamonds generated from carbon sourced from air in the stadium at which the championship game was played. In this example, a mobile carbon capture can be deployed to the stadium prior to a start of the championship game. The mobile carbon capture device can be configured to capture air (e.g., carbon dioxide, nitrogen, argon, etc.) inside the stadium and store the resulting low-purity carbon dioxide mixture within a tank on the mobile carbon capture device. Later, when the mobile carbon capture device returns to the lab, the low-purity mixture can be purified and treated as described above to generate diamonds from carbon extracted from the air in the stadium during the championship game.

11.1 Linking Diamond to Target Location

A diamond can be generated from carbon extracted from an air sample collected at a target location. In one implementation, as shown in FIG. 3, each diamond produced via the method S100 can be identified via a diamond identifier (e.g., a serial number). This serial number can be linked to the location, region, or place from which carbon for a particular diamond was extracted, such that diamond owners or diamond purchasers may have access to this location. For example, diamond purchasers may access a database searchable by serial number of diamonds. Upon entering a particular serial number, a diamond purchaser may identify the location from which the carbon was sourced for the diamond corresponding to this serial number. Additionally and/or alternatively, a future diamond purchaser may search the database by location to identify a set of diamonds generated from carbon sourced from a particular location.

For example, a couple may purchase an engagement ring with a diamond generated from carbon that is sourced from air in a location of significance to the couple (e.g., a place where the couple met, a place where the couple vacationed). In another example, a user (or "partner") may wish to purchase an engagement ring for her partner made from carbon sourced from a location near the Pont des Artes Bridge in Paris. The user may search the database to find a diamond generated from carbon sourced near this location. The user may purchase this diamond and select a setting for the diamond to make an engagement ring. Upon purchasing the diamond, the user may receive a unique serial number specific to this diamond, linking the diamond to the location. Later, the user may propose to her partner at the Pont des Artes Bridge in Paris with this engagement ring including the diamond made from carbon sourced from this location.

The user and the user's partner may later search the database via the unique serial number of the diamond to see when and where carbon for this diamond was sourced.

In another example, players on a winning Superbowl team may receive rings with diamond rings including diamonds generated from carbon sourced from air in the football stadium at which the championship game was played. In this example, a set of carbon capture devices (e.g., mobile carbon capture devices) can be deployed to the football stadium hosting the championship game prior to a start of the game. The carbon capture devices can be configured to filter air and collect carbon dioxide during the Superbowl game. After the game is finished, low purity carbon dioxide mixtures can be collected from each carbon capture device deployed. Then, according to the method S100, these mixtures can be further processed to generate diamonds. Diamond rings can then be made from these diamonds, which may then be distributed to the players of the winning team.

11.1.1 Electronic Sample File

In one implementation, an electronic sample file—including location identifying information—can be generated for an air sample collected at a target location. To track carbon extracted from an air sample collected at a target location throughout the entire diamond generation process, the electronic sample file can be updated throughout this process to include identifiers linked to intermediate products generated from this air sample. In particular, the electronic sample file can include: a location identifier (e.g., a GPS coordinate, an address, a unique identification number linked to the target location) representative of the target location; a set of container identifiers (e.g., barcodes, serial numbers) linked to (e.g., arranged on) containers storing carbon mixtures (e.g., low-purity gaseous mixture, high-purity hydrocarbon mixture) extracted from the air sample collected at the target location; and/or a set of diamond identifiers (e.g., serial numbers, barcodes) linked to diamonds generated from carbon extracted from the air sample collected at the target location.

For example, a carbon capture device can ingest an air sample captured during an air capture period at a target location for collection of a first mixture from the air sample, the first mixture including carbon dioxide and a first concentration of impurities (e.g., nitrogen). This first mixture (i.e., the low-purity carbon dioxide mixture) can be stored in a first container associated with the target location. An electronic sample file can then be generated (e.g., by a user associated with the carbon capture device, by a remote computer system) for the first mixture. A location identifier associated with the target location can be written to the electronic sample file to link the target location to the first mixture. Further, a first identifier arranged on the first container can also be written to the electronic sample file, such that the first container can be stored, shipped to a remote location, and/or further processed and be readily identified as containing the first mixture collected at the target location.

Further, in this example, the first mixture can be collected from the first container and further processed to generate a second mixture including carbon dioxide and a second concentration of impurities less than the first concentration of impurities. The second mixture can then be mixed with a stream of hydrogen in a methanation reactor to generate a first hydrocarbon mixture including hydrocarbons and a third concentration of impurities including nitrogen, carbon dioxide, and hydrogen. This first hydrocarbon mixture can then be collected in a second container. A second identifier arranged on the second container can then be written to the electronic sample file associated with the initial air sample collected at the target location.

Later, this first hydrocarbon mixture—linked to the first location via the second identifier on the second container—can be deposited into a diamond reactor (e.g., a CVD chamber) containing a set of diamond seeds to generate a first set of diamonds. Once the first set of diamonds are generated, the first set of diamonds can be collected from the diamond reactor and stored in a third container. A third identifier arranged on the third container can then be written to the electronic sample file, such that diamonds in the first set of diamonds can be linked to the initial air sample captured at the target location. Additionally and/or alternatively, each diamond in the first set of diamonds can be assigned a diamond identifier. For example, a first diamond, in the first set of diamonds, can be assigned a first diamond identifier (e.g., serial number, SKU). This first diamond identifier—associated with the first diamond in the first set of diamonds—can be written to the electronic sample file.

Additionally, in this implementation, information contained in the electronic sample file can be leveraged to generate a database of diamonds, each diamond in the database linked to a particular location from which carbon for the diamond was initially captured. For example, a first electronic sample file can include: a first location identifier associated with a first target location at which an air sample was collected; a first container identifier arranged on a first container configured to transiently store the low-purity carbon dioxide mixture extracted from the air sample; a second container identifier arranged on a second container configured to transiently store the hydrocarbon mixture generated from the low-purity carbon dioxide mixture; a first diamond identifier associated with a first diamond generated from the hydrocarbon mixture; and a second diamond identifier associated with a second diamond generated from the hydrocarbon mixture. The first electronic sample file can be uploaded to a searchable, online database in Block S190, such that users accessing the online database may search by the first target location to access a list of diamonds—including the first and second diamond—generated from carbon extracted at the first target location.

Additionally, in one variation, Block S180 recites: engraving the first diamond with the first diamond identifier. The first diamond can be engraved with the first diamond identifier stored in the electronic sample file and linking the first diamond, in the first set of diamonds, to the target location. Thus, a user owning or viewing the first diamond may search the database by the first diamond identifier to access information related to location of carbon capture for this first diamond.

In one variation, as described below, the electronic sample file can include additional information related to carbon capture of carbon for a diamond. In particular, the electronic sample file can include information related to: a location of carbon capture; a date or time of carbon capture; and/or a type of a carbon source (e.g., ambient air, human breath) and/or people present near the carbon capture device during the air capture period.

11.2 Time-Based Air Capture

Additionally and/or alternatively, in one variation, a diamond can be generated from carbon extracted from an air sample collected during a particular time period. For example, a user may wish to purchase a diamond generated from carbon extracted from an air sample collected during a particular air capture period such as corresponding to a particular date (e.g., the user's birthday) or a particular event (e.g., a sporting event, a historical event). In this example, the user may search a database to find a diamond generated from carbon sourced during this air capture period.

In one implementation, in which an electronic sample file is generated for the air sample, a timestamp corresponding to the air capture period during which an air sample was collected can be written to an electronic sample file. Additionally and/or alternatively, a set of timestamps corresponding to the air capture period can be written to the electronic sample file for this air sample, such as an initial timestamp corresponding to a start of the air capture period and a final air sample corresponding to an end of the air capture period. As described above, carbon extracted from this air sample can be tracked throughout the process—such as via identifiers linked to the corresponding low-purity gaseous mixture, high-purity gaseous mixture, hydrocarbon mixture—such that each of these intermediate products and the resulting diamond are linked to the timestamp written in the electronic sample file.

Additionally and/or alternatively, in another example, a user may wish to purchase a diamond generated from carbon extracted from an air sample collected at a target location and during a particular air capture period, such as corresponding to a particular date or time period during which the user visited the target location. In this example, both a location identifier corresponding to the target location and a timestamp corresponding to the particular air capture period can be written to an electronic sample file generated for this air sample.

11.3 Source-Based Air Capture

Additionally and/or alternatively, in one variation, the low-purity carbon dioxide mixture can be extracted from air collected from a particular source such that diamonds generated from carbon captured from this air can be linked to the particular source. In particular, an air sample can be collected at a target location from a particular source such as from ambient air, from human breath of a particular person or group of persons, or from carbon dioxide bubbles released from a bottle of champagne.

11.3.1 Source: Ambient Air

In one implementation, carbon can be captured from ambient air. For example, a carbon capture device can be deployed to a target location for carbon capture at this target location. During an air capture period, the carbon capture device can be configured to draw ambient air from a surrounding environment at the target location into the carbon capture device to extract the low-purity gaseous mixture (i.e., carbon dioxide mixture). In one example, the carbon capture device can be deployed outdoors at a popular destination (e.g., Central Park, the Eiffel Tower lawn) and configured to draw ambient air from this environment into the carbon capture device. In another example, the carbon capture device can be deployed indoors such at a wedding venue or a sporting event.

11.3.2 Source: Human Breath

Additionally, in another implementation, carbon can be captured from human breath. For example, a user (e.g., a "future diamond purchaser") may wish to generate a diamond from carbon extracted from the air she breathes. The user may wear a device (e.g., a mask) over her mouth over a period of time (e.g., 30 minutes, 1 hour, 8 hours while sleeping). This device can contain a filter for capturing low-purity carbon dioxide mixture from this user's breath over this period of time. This low-purity carbon dioxide mixture can then be extracted from a filter in this device, and subsequent Blocks of the method can be executed as described above to transform this low-purity carbon dioxide into a diamond, which may then be uniquely linked to this user (and the user's location, a date, and/or a time that this carbon dioxide was captured from the user's breath).

11.3.2.1 Example: Engaged Couple

In another example, an engaged couple may wish to create a diamond for an engagement ring from carbon sourced from both of their breath. The couple may confine themselves to a contained area (e.g., a clean room in a laboratory, an enclosed booth, a room in their house) and a carbon capture device can be located in this contained area. The carbon capture device can filter air in the contained area and extract carbon dioxide from the air, thus collecting air and carbon dioxide from the couple's own breath. Then, the resulting low purity carbon dioxide mixture can be processed according to the method S100 as described above to generate a diamond for this couple's engagement ring.

11.3.2.2 Example: Party Guests

Figure 6:
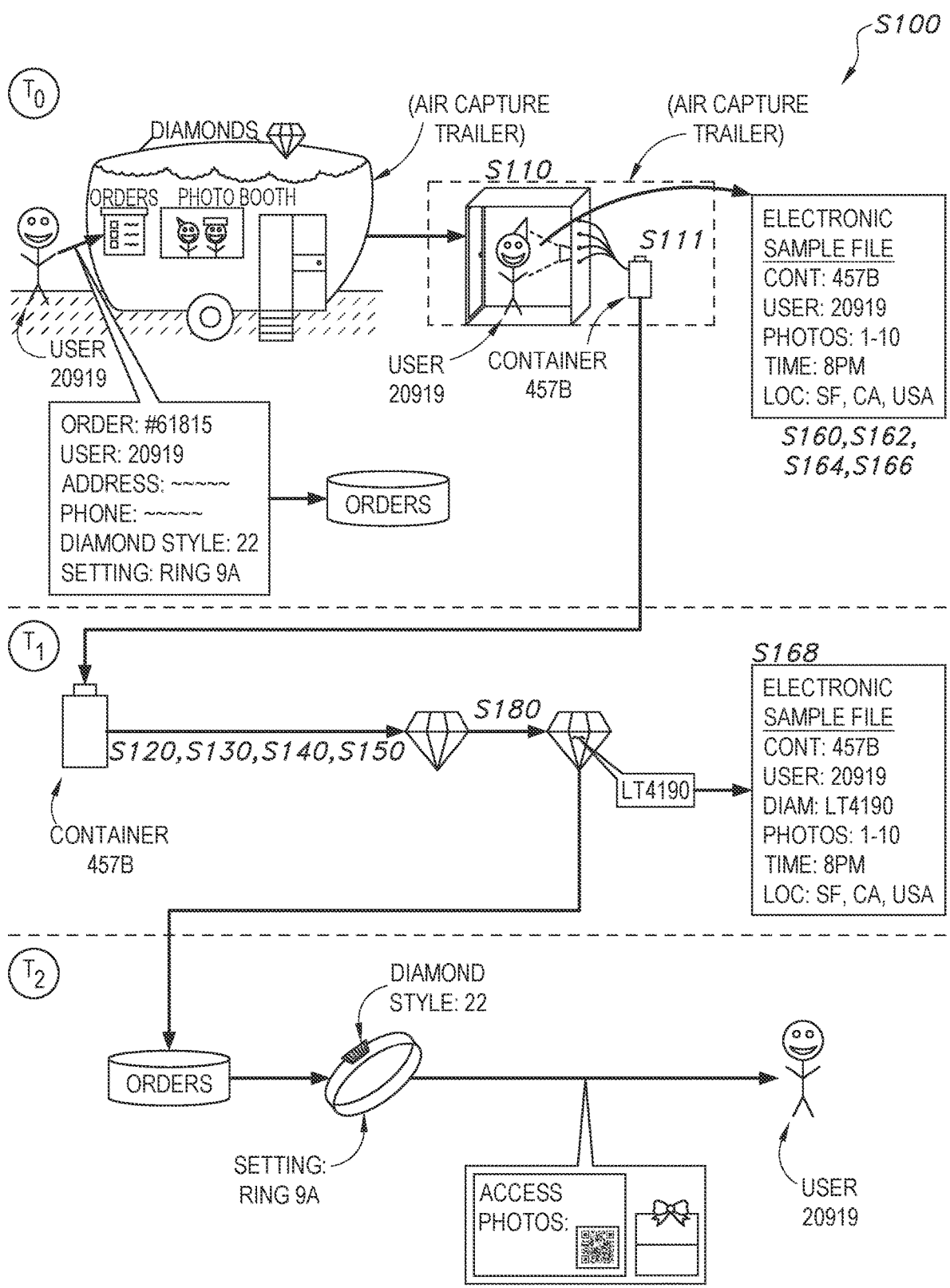
FIG. 6 is a flowchart representation of one variation of the method.

In one example, as shown in FIG. 6, a host or guests of a party (e.g., a wedding, a fundraiser, a holiday party, a special occasion) may wish to create a diamond (or diamonds) from carbon captured from their breath during the party. In this example, the carbon capture device can be deployed to the party (e.g., from a central facility) and installed on a trailer to form a carbon capture trailer. This carbon capture trailer can then be parked and setup at the party (e.g., inside a reception hall, outside in a park) for carbon capture at a target location of the party. To power the carbon capture trailer during the party, the carbon capture trailer can be connected to a lower power grid and/or can be configured to include a set of rooftop solar panels, such as for an outdoor party.

In this example, during the party, guests wishing to generate and/or purchase diamonds from their own breath may: walk into the carbon capture trailer; provide identifying information (e.g., name, phone number, email address); and/or complete order forms for diamonds and settings. The carbon capture trailer can be loaded with a set of air capture cartridges, such that each air sample collected (e.g., from a particular guest or group of guests) can be stored in a separate air capture cartridge linked to a source of the air sample. In particular, each time a new guest or new groups of guests enters the carbon capture trailer, a new (e.g., clean, empty) air capture cartridge can be loaded into the carbon capture device, such that breath from this new guest or new group of guests is collected in the new air capture cartridge.

Further, in this example, the carbon capture trailer can include a photo booth that guests may enter during collection of their breath. The photo booth can be coupled to a first air capture cartridge, such that breath of guests inside the photo booth is routed to and collected within the first air capture cartridge. In particular, a group of guests may sit in the photo booth for a target duration (e.g., 5 minutes, 10 minutes, 30 minutes) while breathing during an air capture period. During this air capture period, the carbon capture device can collect breath of the users (e.g., from within the enclosed photo booth) in the first air capture cartridge while the photo booth captures and stores photos of the group of guests within the photo booth. Additionally, the photo booth can be configured to capture an audio recording of guests during the air capture period. Once the air capture period is complete, an electronic sample file containing guest names (e.g., in the group of guests), a date and/or time of the air capture period, the target location of the party, photos and/or audio recordings captured during the air capture period can be generated. This electronic sample file can then be linked to a cartridge identifier (e.g., QR code, barcode, RFID tag, UUID) corresponding to the first air capture cartridge (e.g., arranged on the first air capture cartridge) containing breath of the group of guests collected during the air capture period.

Once the party is over, contents of the first air capture cartridge can be processed (e.g., at a remote location) further to generate diamonds according to Blocks of the method S100. In this example, contents of each air capture cartridge, in the set of air capture cartridges from the party, can be processed and stored separately. Alternatively, contents of the set of cartridges can be combined and processed as a single air sample from the party.

Each diamond generated from contents of the first air capture cartridge can be engraved with a unique diamond identifier which can then be linked to the electronic sample file. Then, each diamond can be set in a setting (e.g., selected by a guest in the group of guests) to complete a set diamond piece. Each set diamond piece can then be returned to a corresponding guest. For example, a source identifier contained in the electronic sample file including the unique diamond identifier—can be leveraged to access a user profile (e.g., generated from the user order form), in a set of user profiles, including user (e.g., guest) contact information (e.g., name, email address, phone number, shipping address). A notification indicating generation of the diamond and/or set diamond piece can be generated and transmitted to the corresponding user via the set of contact information. Additionally and/or alternatively, the diamond and/or set diamond piece can be directly returned to the corresponding user via the set of contact information.

Further, each set diamond piece can then be returned to a corresponding guests along with: a card containing a web address, a QR code, a username and password, etc., to access contents of the electronic sample file linked to a diamond in the set diamond piece; and a magnification loupe to read the unique diamond identifier from the diamond or setting, which can then be entered into a website (e.g., an online database) to retrieve contents of the electronic sample file linked to the diamond.

Therefore, a guest may leverage the unique diamond identifier on her diamond or setting to access photos and/or audio recordings captured during the air capture period within the photobooth and/or information (e.g., date, time, location, guest names) related to carbon collection for this diamond.

11.3.3 Source: Carbon Dioxide Bubbles

In yet another implementation, carbon can be captured from carbon dioxide gas released in bubbles of a drink (e.g., a carbonated beverage). For example, air can be captured from bubbles released from a bottle of sparkling wine. In this example, an owner of a winery may wish to generate a set of diamonds from carbon captured from carbon dioxide bubbles released from a bottle of sparkling wine produce by the winery. The user may place the bottle of sparkling wine in a contained space (e.g., container) and the carbon capture device can be configured to draw air from within the contained space. Then, when the owner opens the bottle of sparkling wine and carbon dioxide bubbles are released, the carbon capture device can draw this carbon dioxide gas— mixed with ambient air from the contained space—into the carbon capture device. Then, the resulting carbon dioxide mixture can be processed according to the method S100 as described above to generate a set of diamonds for the owner, employees and/or patrons of this winery.

In each of these implementations, a source identifier corresponding to a carbon source (e.g., ambient air, human breath, carbon dioxide bubbles) can be written to the electronic sample file for the air sample. Thus, in one example, a user may search a database for a diamond generated from carbon captured from: a particular common space (e.g., a park) by entering (e.g., selecting from a list or typing into the database) a source identifier corresponding to ambient air collected at this particular common space; the user's own breath by entering a source identifier unique to human breath captured from this user; or a particular bottle of a sparkling beverage by entering a source identifier unique to carbon captured from carbon dioxide gas released from this particular bottle.

11.4 Permanent or Semi-Permanent Deployment

In one implementation, the carbon capture device can be permanently and/or semi-permanently deployed to a target location and configured to capture carbon from air samples collected at this target location. For example, the carbon capture device can be mounted to an existing building or structure or installed in a public space or within a commercial store such that users may visit and/or access the carbon capture device.

In this implementation, the carbon capture device can be configured to collect air samples at this target location continuously, at regular intervals (e.g., once per hour, once per day, once per week), and/or responsive to an input by a user (e.g., manually). The carbon capture device can be configured to collect these air samples over an air capture period of a target duration (e.g., 10 minutes, 30 minutes, 1 hour, 24 hours, 1 week).

11.4.1 Example: Park Installation

For example, a carbon capture device can be semi-permanently installed in a park (e.g., a heavily trafficked park). The carbon capture device can be configured to collect air samples at this park daily, such as collecting an air sample each day over a 12-hour period during which the park is open to the public. Each day, during this 12-hour period, the carbon capture device can be configured to continuously or semi-continuously draw air from the park through a set of inlets (e.g., one inlet, three inlets, ten inlets) of the carbon capture device.

Further, the carbon capture device can be configured to include a set of containers, each container configured to collect a volume of a low-purity carbon dioxide mixture and corresponding to a particular day of the week. At an end of the week, the set of containers can be removed from the carbon capture device (e.g., while at the park) and transported to a remote facility for processing according to Blocks of the methods S100. A fresh (e.g., clean) set of containers can then be installed in the carbon capture device to replace the previous set of containers. Each container, in the set of containers, can be linked to this park and to a time period of collection of the air sample, such that users (e.g., guests visiting the park) may locate and/or purchase diamonds generated from carbon captured from this park during a particular time period.

In particular, a user may wish to visit the park so that she may eventually purchase a diamond generated from carbon captured at the park during a particular time period corresponding to her visit at the park. During the particular time period, the carbon capture device can draw ambient air from the park into the set of inlets of the carbon capture device for extraction and storage of a volume of the low-purity carbon dioxide mixture into a first container, in the set of containers. During installation of the set of containers and/or upon collection of the set of containers, an electronic sample file can be generated including: a first container identifier corresponding to the first container; a first location identifier corresponding to the park; and a first timestamp corresponding to a particular air capture period—including the particular time period during which the user visited the park—during which the volume of the low-purity carbon dioxide mixture in the first container was collected.

Later, once the volume of the low-purity carbon dioxide mixture in the first container is converted to a set of diamonds, a unique diamond identifier can be assigned to each diamond, in the set of diamonds, to generate a set of diamond identifiers. The set of diamond identifier can then be written to the electronic sample file. The user may then find and locate a first diamond, in the set of diamonds, that she wishes to purchase by searching an online database by location (i.e., the first location identifier) and time (i.e., the first timestamp) to locate the first set of diamonds generated from carbon captured during the user's visit at the park.

11.4.2 Example: Carbon Capture Booth

In another example, a carbon capture device can be semi-permanently installed in a target location as a carbon capture booth (e.g., an enclosed booth, a "phone booth") configured to collect human breath from a particular user or a particular set of users for a target duration.

In particular, in this example, a user may wish to purchase a diamond generated from carbon captured from her own breath. The user may enter the booth and place a mask contained in the booth over her mouth to initiate collection of the low-purity carbon dioxide mixture from her breath. In this example, the carbon capture device can include a user interface configured to collect user information (e.g., name, contact information) and/or provide instructions to the user.

The carbon capture device can be configured to draw the user's breath into the carbon capture device for extraction of the low-purity carbon dioxide mixture for a target duration (e.g., 10 minutes, 30 minutes, 1 hour). The carbon capture device can collect this low-purity carbon dioxide mixture in a first container, in a set of containers, including a first container identifier (e.g., barcode, serial number, identification number) arranged on a surface of the first container. In response to expiration of the target duration, the user interface of the carbon capture device can render a code for the user to later track her sample of the low-purity carbon dioxide mixture throughout processing and/or to locate a diamond generated from this sample. Additionally and/or alternatively, the user interface can be configured to output a receipt including the code for the user to take with her.

11.5 Transient Deployment

In another implementation, the carbon capture device can be transiently deployed to a target location, such as for a particular event of a fixed duration. For example, the carbon capture device can be deployed to the target location for a fixed duration and returned to a central facility—carrying a set of containers of the low-purity carbon dioxide mixture collected at the target location—for processing of the low-purity carbon dioxide mixture to generate diamonds. Similarly, in this implementation, the carbon capture device can be configured to: collect air samples at this target location continuously, at regular intervals (e.g., once every 10 minutes, once every 30 minutes, once per hour, once per a duration of an associated event), and/or responsive (e.g., manually) to an input by a user associated with the carbon capture device; and collect these air samples over an air capture period of a target duration (e.g., 10 minutes, 30 minutes, 1 hour, a duration of an associated event).

11.5.1 Example: Carbon Capture at a Party

For example, a primary user may wish to purchase a necklace with a diamond generated from carbon that is sourced from air (e.g., ambient air, human breath) collected during her wedding reception in a particular venue. Prior to the wedding reception, the carbon capture device can be deployed to the venue for setup. During the wedding reception, the carbon capture device can be configured to continuously or semi-continuously draw air from the venue through an inlet of the carbon capture device for collection of a volume of the low-purity carbon dioxide mixture into a set of containers (e.g., one or more containers).

Additionally and/or alternatively, the carbon capture device can be configured to capture a volume of the low-purity carbon dioxide from breath of users (e.g., guests) attending the wedding reception at the venue. In particular, a user (e.g., a guest) may wear a device (e.g., mask) over his mouth over an air capture period of a fixed duration (e.g., 1 minute, 5 minutes, 20 minutes). The device can include a filter configured to capture the low-purity carbon dioxide mixture from the user's breath. The user may then enter or receive a unique source identifier (e.g., a name of the user, an email address of the user, a unique code generated for the user) associated with this user and linked to a container storing the low-purity carbon dioxide mixture collected from this user's breath. In this example, the carbon capture device can be configured to store the low-purity carbon dioxide mixture collected from the this user's breath in a container unique to this user's breath (e.g., a personal container) or in a container configured to store a low-purity carbon dioxide mixture collected from multiple or all guests attending the party.

Throughout the fixed duration of the wedding reception, the carbon capture device can continue to capture low-purity carbon dioxide mixtures from breath of additional users wearing the device. Each of these users may receive a unique source identifier associated with the user and linked to a container, in a set of containers, storing the low-purity carbon dioxide mixture collected from the user's breath.

Additionally, each container, in the set of containers, can include a unique container identifier (e.g., a barcode, a serial number) arranged on the container. These container identifiers can then be written to an electronic sample file generated for carbon captured during the wedding reception. Further, the electronic sample can include: a location identifier linked to a location of the venue (e.g., an address, a geographic region, a name of the venue); a timestamp corresponding to a time period during which the wedding reception occurred; a set of source identifiers, each source identifier linked to a particular user and a particular container identifier arranged on a particular container, in the set of containers, storing a volume of the low-purity carbon dioxide mixture collected from the particular user's breath. Therefore, by linking the low-purity carbon dioxide mixture and resulting diamonds to the location identifier, the set of source identifiers, and the timestamp, the primary user may later locate and purchase a diamond, from the set of diamonds, generated from carbon captured from ambient air and breath of her wedding guests during the wedding reception at the venue. Further, other users (e.g., wedding guests) may later locate and/or purchase diamonds generated from carbon captured from each of their own breath.

Once the wedding reception is over, each container, in the set of containers, storing a volume of the low-purity carbon dioxide mixture can be transported to a remote facility for further processing according to Blocks of the method S100. For example, the carbon capture device—including the set of containers—can be returned to a processing facility. The set of containers can be removed from the carbon capture device for processing according to Blocks of the method S100 at the processing facility and/or shipped to a secondary location for additional processing. The carbon capture device can then be loaded with a second set of clean (e.g., empty) containers and prepared for redeployment to a different location.

As a person skilled in the art will recognize from the previous detailed description and from the figures and claims, modifications and changes can be made to the embodiments of the invention without departing from the scope of this invention as defined in the following claims.

We claim:

1. A method comprising:
   ingesting a first air sample, collected during an air capture period and defining a volume exceeding a threshold volume, to extract a first mixture comprising carbon dioxide and a first concentration of impurities comprising nitrogen;
   conveying the first mixture through a first liquefaction unit configured to remove impurities from the first mixture to generate:
      a first exhaust stream comprising impurities comprising nitrogen; and
      a second mixture comprising carbon dioxide and a second concentration of impurities less than the first concentration of impurities;
   in a methanation reactor, mixing the second mixture with a stream of hydrogen to generate a first hydrocarbon mixture comprising hydrocarbons and a third concentration of impurities comprising nitrogen, carbon dioxide, and hydrogen;
   conveying the first hydrocarbon mixture through a second liquefaction unit configured to remove impurities from the second hydrocarbon mixture to generate:
      a second exhaust stream comprising impurities; and
      a second hydrocarbon mixture comprising hydrocarbons and a fourth concentration of impurities less than the third concentration of impurities; and
   depositing the second hydrocarbon mixture in a diamond reactor containing a set of diamond seeds to generate a first set of diamonds via chemical vapor deposition.

2. The method of claim 1, wherein conveying the first hydrocarbon mixture through the second liquefaction unit to generate the second hydrocarbon mixture comprises conveying the first hydrocarbon mixture through the second liquefaction unit to generate the second hydrocarbon mixture comprising the fourth concentration of impurities comprising less than one percent and comprising nitrogen comprising less than 1.2 parts-per-billion.

3. The method of claim 1, further comprising:
   conveying the second hydrocarbon mixture from an outlet of the second liquefaction unit through a compressor, the second hydrocarbon mixture comprising:
      a first concentration of methane at an inlet of the compressor; and
      a second concentration of methane greater than the first concentration of methane at an outlet of the compressor;
   conveying the second hydrocarbon mixture from the outlet of the compressor through a filter cartridge configured to extract impurities comprising nitrogen from the second hydrocarbon mixture, the second hydrocarbon mixture comprising a third concentration of methane greater than the second concentration of methane at an outlet of the filter cartridge; and
   wherein depositing the second hydrocarbon mixture in the diamond reactor comprises transferring the second hydrocarbon mixture from the filter cartridge to within the diamond reactor.

4. A method comprising:

ingesting a first air sample collected during an air capture period to extract a first carbon dioxide mixture comprising a first concentration of impurities comprising nitrogen;

transferring the first carbon dioxide mixture into a liquefaction unit configured to remove impurities from the first carbon dioxide mixture to generate:
- a first exhaust stream comprising impurities comprising nitrogen; and
- a second carbon dioxide mixture comprising a second concentration of impurities less than the first concentration of impurities;

in a methanation reactor, mixing the second carbon dioxide mixture with a stream of hydrogen to generate a first hydrocarbon mixture comprising a third concentration of impurities comprising carbon dioxide, hydrogen, and water;

conveying the first hydrocarbon mixture through a set of filters configured to capture impurities comprising hydrogen and carbon dioxide from the first hydrocarbon mixture to generate a second hydrocarbon mixture comprising a fourth concentration of impurities less than the third concentration of impurities; and depositing the second hydrocarbon mixture in a diamond reactor containing a set of diamond seeds to generate a first set of diamonds via chemical vapor deposition, the second hydrocarbon mixture comprising:
- the fourth concentration of impurities less than five percent and comprising nitrogen comprising less than 1.2 parts-per-billion; and
- a concentration of methane greater than ninety-five percent.

5. The method of claim 4, wherein conveying the first hydrocarbon mixture through the set of filters comprises:

conveying the first hydrocarbon mixture from the methanation reactor and through a first membrane filter configured to capture impurities comprising carbon dioxide and hydrogen from the first hydrocarbon mixture; and conveying the first hydrocarbon mixture from the first membrane filter through a second filter unit configured to capture impurities comprising nitrogen from the first hydrocarbon mixture to generate the second hydrocarbon mixture.

6. The method of claim 4:

wherein ingesting the first air sample collected during the air capture period to extract the first carbon dioxide mixture further comprises:
- during the air capture period, collecting the first air sample at a target location, the first air sample comprising a first concentration of carbon dioxide;
- extracting a first amount of carbon dioxide from the first air sample via filtration of the first air sample; and
- in a chamber, heating the first amount of carbon dioxide to generate the first mixture comprising a second concentration of carbon dioxide greater than the first concentration of carbon dioxide;

wherein transferring the first carbon dioxide mixture into the liquefaction unit comprises storing the first carbon dioxide mixture into a first container configured to promote liquefaction of the first carbon dioxide mixture;

further comprising transporting the first container from the target location to a secondary location; and wherein mixing the second carbon dioxide mixture with the stream of hydrogen to generate the first hydrocarbon mixture in the methanation reactor comprises, at the secondary location:
- ingesting a volume of the second carbon dioxide mixture from the first container; and
- mixing the volume of the second carbon dioxide mixture with the stream of hydrogen to generate the first hydrocarbon mixture in the methanation reactor.

7. The method of claim 6, further comprising:

generating an electronic sample file;

writing a location identifier corresponding to the target location to the electronic sample file;

writing a timestamp corresponding to the air capture period to the electronic sample file;

writing a first identifier arranged on the first container to the electronic sample file; and writing a diamond identifier, corresponding to a first diamond in the first set of diamonds, to the electronic sample file.

8. A method comprising:

ingesting a first air sample, collected during an air capture period and defining a volume exceeding a threshold volume, to extract a first mixture comprising carbon dioxide and a first concentration of impurities comprising nitrogen;

conveying the first mixture through a first liquefaction unit configured to remove impurities from the first mixture to generate:
- a first exhaust stream comprising impurities comprising nitrogen; and
- a second mixture comprising carbon dioxide and a second concentration of impurities less than the first concentration of impurities;

in a methanation reactor, mixing the second mixture with a stream of hydrogen to generate a first hydrocarbon mixture comprising hydrocarbons and a third concentration of impurities comprising nitrogen, carbon dioxide, and hydrogen;

conveying the first hydrocarbon mixture through a second liquefaction unit configured to remove impurities from the second hydrocarbon mixture to generate:
- a second exhaust stream comprising impurities; and
- a second hydrocarbon mixture comprising hydrocarbons and a fourth concentration of impurities less than the third concentration of impurities; and depositing the second hydrocarbon mixture in a reactor to generate a solid carbon product.

9. The method of claim 8, wherein conveying the first hydrocarbon mixture through the second liquefaction unit to generate the second hydrocarbon mixture comprises conveying the first hydrocarbon mixture through the second liquefaction unit to generate the second hydrocarbon mixture comprising the fourth concentration of impurities comprising less than one percent and comprising nitrogen comprising less than 1.2 parts-per-billion.

10. The method of claim 8, further comprising:

conveying the second hydrocarbon mixture from an outlet of the second liquefaction unit through a compressor, the second hydrocarbon mixture comprising:
- a first concentration of methane at an inlet of the compressor; and
- a second concentration of methane greater than the first concentration of methane at an outlet of the compressor;

conveying the second hydrocarbon mixture from the outlet of the compressor through a filter cartridge configured to extract impurities comprising nitrogen from the second hydrocarbon mixture, the second hydrocarbon mixture comprising a third concentration of methane greater than the second concentration of methane at an outlet of the filter cartridge; and wherein depositing the second hydrocarbon mixture in the reactor comprises transferring the second hydrocarbon mixture from the filter cartridge to within the reactor.

11. The method of claim 8, wherein depositing the second hydrocarbon mixture in the reactor to generate the solid carbon product comprises depositing the second hydrocarbon mixture in the reactor to generate a first set of diamonds via chemical vapor deposition.

12. A method comprising:
ingesting a first air sample collected during an air capture period to extract a first carbon dioxide mixture comprising a first concentration of impurities comprising nitrogen;
transferring the first carbon dioxide mixture into a liquefaction unit configured to remove impurities from the first carbon dioxide mixture to generate:
a first exhaust stream comprising impurities comprising nitrogen; and
a second carbon dioxide mixture comprising a second concentration of impurities less than the first concentration of impurities;
in a methanation reactor, mixing the second carbon dioxide mixture with a stream of hydrogen to generate a first hydrocarbon mixture comprising a third concentration of impurities comprising carbon dioxide, hydrogen, and water;
conveying the first hydrocarbon mixture through a set of filters configured to capture impurities comprising hydrogen and carbon dioxide from the first hydrocarbon mixture to generate a second hydrocarbon mixture comprising a fourth concentration of impurities less than the third concentration of impurities; and
depositing the second hydrocarbon mixture in a reactor to generate a solid carbon product.

13. The method of claim 12, wherein conveying the first hydrocarbon mixture through the set of filters comprises:
conveying the first hydrocarbon mixture from the methanation reactor and through a first membrane filter configured to capture impurities comprising carbon dioxide and hydrogen from the first hydrocarbon mixture; and
conveying the first hydrocarbon mixture from the first membrane filter through a second filter unit configured to capture impurities comprising nitrogen from the first hydrocarbon mixture to generate the second hydrocarbon mixture.

14. The method of claim 12:
wherein ingesting the first air sample collected during the air capture period to extract the first carbon dioxide mixture further comprises:
during the air capture period, collecting the first air sample at a target location, the first air sample comprising a first concentration of carbon dioxide;
extracting a first amount of carbon dioxide from the first air sample via filtration of the first air sample; and
in a chamber, heating the first amount of carbon dioxide to generate the first mixture comprising a second concentration of carbon dioxide greater than the first concentration of carbon dioxide;
wherein transferring the first carbon dioxide mixture into the liquefaction unit comprises storing the first carbon dioxide mixture into a first container configured to promote liquefaction of the first carbon dioxide mixture;
further comprising transporting the first container from the target location to a secondary location; and
wherein mixing the second carbon dioxide mixture with the stream of hydrogen to generate the first hydrocarbon mixture in the methanation reactor comprises, at the secondary location:
ingesting a volume of the second carbon dioxide mixture from the first container; and
mixing the volume of the second carbon dioxide mixture with the stream of hydrogen to generate the first hydrocarbon mixture in the methanation reactor.

15. The method of claim 14, further comprising:
generating an electronic sample file;
writing a location identifier corresponding to the target location to the electronic sample file;
writing a timestamp corresponding to the air capture period to the electronic sample file;
writing a first identifier arranged on the first container to the electronic sample file; and
writing a product identifier, corresponding to the solid carbon product, to the electronic sample file.

16. The method of claim 12, wherein depositing the second hydrocarbon mixture in the reactor to generate the solid carbon product comprises depositing the second hydrocarbon mixture in the reactor to generate a first set of diamonds via chemical vapor deposition.

\* \* \* \* \*